United States Patent [19]
de la Huerga

[11] Patent Number: 6,032,155
[45] Date of Patent: Feb. 29, 2000

[54] SYSTEM AND APPARATUS FOR ADMINISTERING PRESCRIBED MEDICATION TO A PATIENT

[76] Inventor: Carlos de la Huerga, 9190 N. Upper River Rd., River Hills, Wis. 53217

[21] Appl. No.: 08/955,475

[22] Filed: Oct. 21, 1997

Related U.S. Application Data

[63] Continuation-in-part of application No. 08/834,634, Apr. 14, 1997, Pat. No. 5,960,085.

[51] Int. Cl.$^7$ .................................................. G06F 17/30
[52] U.S. Cl. .................................... 707/104; 364/479.14
[58] Field of Search ................................ 707/9, 10, 104; 221/2, 4; 364/479.06, 479.07, 479.11, 479.14, 479.01, 479.02; 702/177

[56] References Cited

U.S. PATENT DOCUMENTS

| | | | |
|---|---|---|---|
| Re. 35,743 | 3/1998 | Pearson | 221/2 |
| 4,664,289 | 5/1987 | Shimizu et al. | 221/2 |
| 4,732,411 | 3/1988 | Siegel | 283/75 |
| 4,733,362 | 3/1988 | Haraguchi | 364/479 |
| 4,785,969 | 11/1988 | McLaughlin | 221/2 |
| 4,823,982 | 4/1989 | Aten et al. | 221/3 |
| 4,839,806 | 6/1989 | Goldfischer et al. | 364/413.02 |
| 4,847,764 | 7/1989 | Halvorson | 364/413.02 |
| 4,857,713 | 8/1989 | Brown | 235/375 |
| 4,857,716 | 8/1989 | Gombrich | 235/462 |
| 5,014,875 | 5/1991 | McLaughlin | 221/2 |
| 5,208,762 | 5/1993 | Charbut | 364/478 |
| 5,213,232 | 5/1993 | Kraft et al. | 221/277 |
| 5,273,318 | 12/1993 | Gorman | 235/375 |
| 5,401,059 | 3/1995 | Ferrario | 283/67 |
| 5,405,048 | 4/1995 | Rogers et al. | 221/211 |
| 5,460,294 | 10/1995 | Williams | 221/2 |
| 5,480,062 | 1/1996 | Rogers et al. | 221/174 |
| 5,502,944 | 4/1996 | Kraft et al. | 53/55 |
| 5,508,499 | 4/1996 | Ferrario | 235/375 |
| 5,522,525 | 6/1996 | McLaughlin et al. | 221/4 |
| 5,745,366 | 4/1998 | Higham | 364/479.12 |
| 5,826,217 | 10/1998 | Lerner | 702/177 |
| 5,852,590 | 12/1998 | De La Huerga | 368/10 |

*Primary Examiner*—Thomas G. Black
*Assistant Examiner*—John C. Loomis
*Attorney, Agent, or Firm*—Jeffrey S. Sokol; Sokol Law Offices

[57] ABSTRACT

This invention relates to a method and apparatus for administering prescribed medication to a patient. The prescribed medication administration system and apparatus dispense prescribed medication, verify the medication is given to a correct patient by an authorized healthcare worker and tracks and records the administration of the medication. The system utilizes a workstation connected to a database containing prescribed medication dose information for various patients. A healthcare worker uses the workstation to manually or automatically dispenses the medication the portable container. An information device is secured to the portable container during transport and administration of the medication to the intended patient. The information device prevents access to the medication or warns the healthcare worker of a potential error if the medication is delivered to the wrong patient or administered by an unauthorized healthcare worker. The information device records actual consumption information, and delivers this information back the workstation database or to a hospital or pharmacy database.

68 Claims, 20 Drawing Sheets

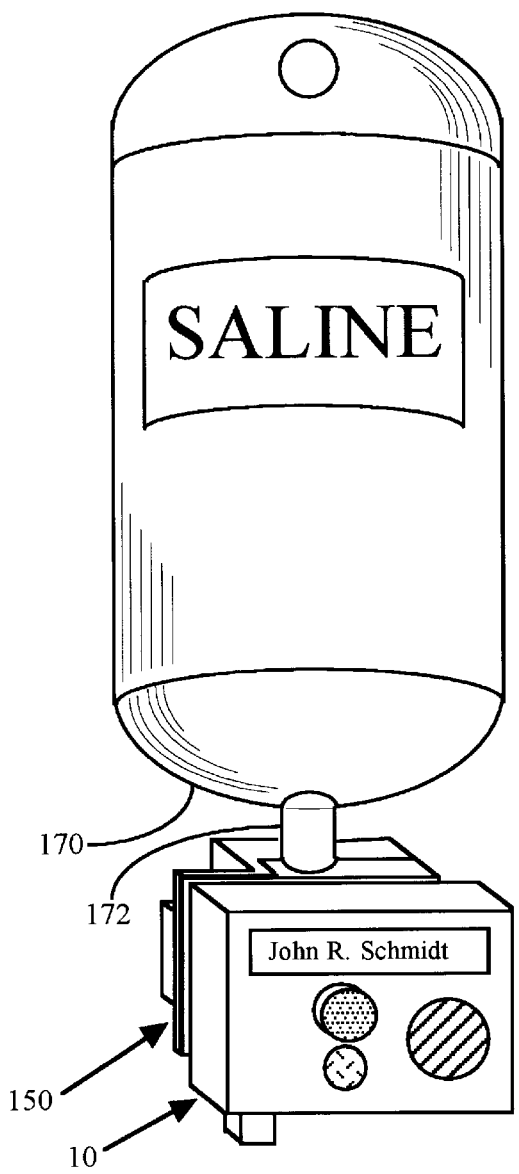
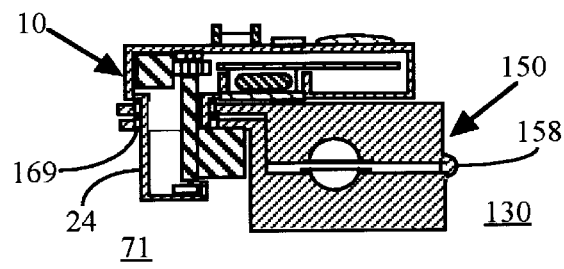
Figure 8
Figure 7
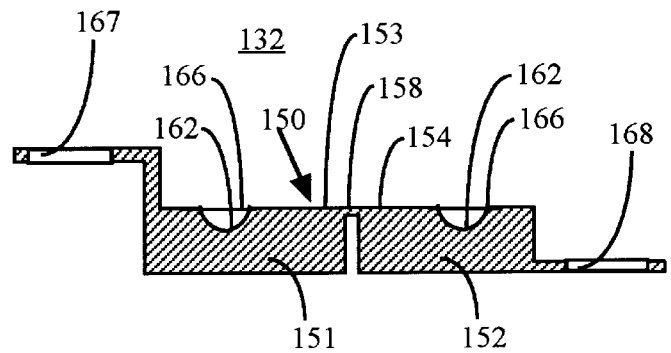
Figure 9

| | |
|---|---|
| 500 | Memory Contents -- Information Device 10 |
| 504<br>505<br>506<br>507 | Information Device Data Elements<br>    Serial Number of Information Device<br>    End of Life for Battery<br>    Communication Encryption Codes |
| 520<br>540<br>560<br>580<br>600 | Information Received from Dispensing System 200, 280<br>    Selected Patient Information<br>    Selected Prescribed Medication Dose Information<br>    Predetermined Healthcare Worker Information<br>    Dispensed Medication Information<br>    Medication Report Components |
| 621 | Information Received from Patient Identification Device 300<br>    Specific Patient Information |
| 681<br>621 | Information Received from Healthcare Worker Identification Device 320<br>    Administering Healthcare Worker Information<br>    Specific Patient Information |
| 621 | Information Received from Patient Room Workstation 350 or<br>Computer Peripheral Device 355<br>    Specific Patient Information |
| 640<br>642<br><br>643<br>644<br>660 | Information Created when Container 100 opened<br>    Consumption Information:<br>        Consumption Tiem Information/Date and time portable<br>        container opened<br>        Amount of Medication offered to Patient<br>        Amount of Medication Patient Consumed<br>    Final Transaction Medication Report |

Figure 17

| | |
|---|---|
| 700 | Patient Medication Information -- Dispensing Workstation 200, 280 |
| 520 | Selected Patient Information |
| 521 | Patient Identification Number |
| 522 | Patient Name |
| 523 | Admitting Physician |
| 524 | Patient Room Number |
| 525 | Patient Blood Type |
| 540 | Selected Prescribed Medication Dose Information for each Medication Prescribed |
| 541 | Medication Type Prescribed |
| 542 | Medication Quantity Prescribed |
| 543 | Dosing Times |
| 544 | Identification of Physician Prescribing Medication |
| 560 | Predetermined Healthcare Worker Information |
| 561 | Responsibilities/Title Of Healthcare Worker Allowed to Give Medication |
| 562 | Healthcare Worker Identification Number(s) Allowed to Give Medication |
| 563 | Healthcare Worker Name(s) Allowed to Give Medication |
| 564 | List of Patients Under Care of each Healthcare Worker |

Figure 18

| | |
|---|---|
| 580 | Dispensed Medication Information -- Dispensing Workstation 200, 280 |
| 581 | Medication Information |
| 582 | Date and Time Medication Dispensed |
| 583 | Identification of Healthcare Worker who dispensed Medication |
| 584 | Type and Quantity Actually Dispensed |
| 600 | Medication Report Components |
| 720 | Medication Report |
| 724 | Universal Record Locator |

Figure 19

| 620 | Memory Contents -- patient identification device 300 |
|---|---|
| 621 | Specific Patient Information |
| 622 |     Patient Identification Number |
| 623 |     Patient Name |
| 624 |     List of Medications to which Patient is Allergic |
| 625 |     Admitting Physician |
| 626 |     Patient Blood Type |

Figure 20

| 680 | Memory Contents -- Healthcare Worker Identification Device 320 |
|---|---|
| 681 | Administering Healthcare Worker Information |
| 682 |     Responsibilities/Title |
| 683 |     Identification Number |
| 684 |     Name |
| 685 |     List of Patients Under Care of Healthcare Worker |
| | Information Received from patient identification device 300 |
| 621 | Specific Patient Information |
| | Information Received from Information Device 10 |
| 660 | Final Medication Transaction Report |

Figure 21

| 690 | Memory Contents -- Patient Room Information Workstation 350 or Computer Peripheral Device 355 |
|---|---|
| 621 | Specific Patient Information |
| | Information Received from Information Device 10 |
| 660 | Final Medication Transaction Report |

Figure 22

| 660 | Final Medication Transaction Report |
|---|---|
| 520 | Selected Predetermined Patient Information |
| 540 | Selected Prescribed Medication Dose Information |
| 560 | Predetermined Healthcare Worker Information |
| 580 | Dispensed Medication Information |
| 621 | Specific Patient Information |
| 680 | Administering Healthcare Worker Information |
| 640 | Consumption Information: |
| 670 |     Medication Report Components |
| 730 |         Medication Report |
| 734 |         Universal Record Locator |

Figure 23

```
<html>
<body>
<a href="http://hww.st._mary.springfield/demographics/987654321/19_May_1996">
ID: 987654321</a><br>
Date: 13:59 19-May-1996<br>
Report type: Medication Administration<br>
Patient ID Verified: YES<br>
<br>
Medication Given:<br>
Penicillin              100mg          2 capsules<br>
Tylenol w/Codeine    200mg         1 capsules<br>
<br>
Given by: Mary T. Adamson, R.N.,   at: 13:59 19-May-1996<br>
Dispensed by: Sam W. Johnston, R.N.,   at: 13:42 19-May-1996<br>
<br>
ID Device Serial Number: 1265338<br>
</html>
```

Figure 26 hww.st_mary.springfield/medication/given/987654321/19_May_1996/13:42

Figure 27

ID: 987654321
Date: 13:59 19-May-1996
Report type: Medication Administration
Patient ID Verified: YES Medication Given:
Penicillin              100mg          2 capsules
Tylenol w/Codeine    200mg         1 capsules Given by: Mary T. Adamson, R.N.,   at: 13:59 19-May-1996
Dispensed by: Sam W. Johnston, R.N.,   at: 13:42 19-May-1996

ID Device Serial Number: 1265338

Figure 28

PATIENT VERIFICATION SYSTEM

800

Medication 110 for a selected patient is dispensed into Portable Container 100. Medication Dispensing Machine 204 or Medication Dispensing Workstation 220 transmits a dispensing signal containing selected patient information 520 to Information Device 10.

804

Transport Information Device 10 and Portable Container 100 filled with doses of medication 110 to specific Patient 360. Information Device 10 containing selected patient information 520 is associated with a Patient Identification Device 300 containing specific patient information 621.

808

Healthcare worker 330 presses activation button 16 on Information Device 10. Identification device 10 sends a request for data.

812

Patient identification device 300 receives the request and sends a message that contains specific patient identification information 621.

816

Information Device 10 receives specific patient information 621 and compares it with the selected patient information 520.

MEDICATION TRACKING SYSTEM

910 —

Medication 110 for a selected patient is dispensed into Portable Container 100.

914 —

Transport Information Device 10 and Portable Container 100 filled with doses of medication 110 to be given to specific patient 360. Information Device 10 containing predetermined healthcare information 560 is associated with Healthcare Worker Identification Device 320 containing administering healthcare worker information 681

920 —

Healthcare worker 330 presses activation button 16 on information device 10. Information device 10 sends a request for data.

924 —

Healthcare worker identification device 320 receives the request and sends a message that contains the administering healthcare worker information 681.

928 —

Identification device 10 receives administering healthcare worker information 681 and adds it to memory contents 500 and formats initial medication report 720 into medication report 730 to include administering healthcare worker information 681 in field 726.

SYSTEM AND APPARATUS FOR ADMINISTERING PRESCRIBED MEDICATION TO A PATIENT

This application is a contination-in-part of U.S. application Ser. No. 08/834,634, filed Apr. 14, 1997 and now U.S. Pat. No. 5,960,085.

TECHNICAL FIELD OF THE INVENTION

This invention relates to a system and apparatus for dispensing a prescribed dose of medication, tracking and verifying that the medication is administered to a specific patient, automatically recording the time the medication is dispensed, the time the medication is administered, the type and amount of medication being administered, identifying the health care worker administering the medication, and returning this information to a hospital or pharmacy database.

BACKGROUND OF THE INVENTION

Medication prescribed by a physician in a hospital for a patient can be dispensed either manually by a pharmacist or by a unit dose dispensing system in the pharmacy or placed at various locations in the hospital for nurses to use. In the case of manual dispensing, a medication order is sent to the pharmacy where the correct medication is selected or formulated. The medication is then placed in a container, plastic bag, or envelope which is in turn labeled with identification information specifying the patient that is to receive the medication as well as information about the medication dispensed. Such labeling can be achieved by the use of a marking pen or a computer printer adhesive label.

A variety of devices have been invented and several placed in commercial production for the dispensing of unit dosages of medication. These systems are often designed to be placed in a variety of locations in a hospital for local and convenient dispensing of medications. A key advantage of these systems is a reduction in time and labor in the delivery of prescribed medication to a patient. Without such systems, each prescribed medication must be dispensed by the central hospital pharmacy, labeled, and transported to the nurses station near the patient's room. This process must be done 24 hours a day and the dispensing must be done in anticipation of when each new dosage is due with an allowance for time spent in transit. Unit dosage dispensing systems usually have a tray or cartridge that is loaded with multiple dosages of medication by the central pharmacy. This tray or cartridge is then carried to the unit dosage dispensing system where it is inserted, along with information regarding the medication in the tray or cartridge. This information usually includes the medication name and the number of doses contained. When a patient is to receive medication the nurse usually must use a mechanical key, an electronic key, or a computer password to gain access to the dispensing process. The nurse will identify the medication and may identify the patient to receive the medication. The dispensing system then locates the correct tray or cartridge containing the desired medication and then removes one or more doses of the medication as required, typically delivering them to a drawer or door that the nurse may open to remove the medication.

After dispensing the nurse carries the medication to the patient for consumption. The dispensing system can keep track of the date and time when the medication was dispensed, for which patient it was for, and possibly the nurse to whom it was dispensed. However, the dispensing system cannot determine if the medication was in fact given, if it was given later, who gave it to the patient, or if it was given to the correct patient.

Several studies have documented that most medications in a hospital are given to the correct patient. However, the small percentage of medications that are given to the wrong patient is cause for great concern. This can happen if a patient is moved from one room to another and a new patient is now in the former patient's bed. Occasionally, the former patient's name may be left written on a board near the bed or by the doorway. While nurses are suppose to verify the patient's name or identification number written on a bracelet each time they administer a medication, this may not always happen. The nurse may receive a call to go to an emergency while giving a medication and thus be rushed, the patient may be unable to speak to identify themselves, or the nurse may not want to disturb a patient who is sleeping. Errors in giving medication to the wrong patient can cause a variety of reactions that can sometimes lead to death.

To track when a patient was given medication and who gave it, hospitals employ either manual or computerized recording systems. Manual systems are time consuming and can cause errors in patient billing. Even with computerized record systems, the nurse must spend some amount of time entering and verifying the information. It is claimed that within a hospital that over 60% of all expenses are related to nursing, and of that nearly half of this is for nurses to fill out paperwork and write observations. With continuing efforts to control the rising cost of providing health care, hospitals need to explore all methods possible to reduce nurse time spent away from directly caring for patients.

The present invention is intended to solve these and other problems.

BRIEF DESCRIPTION OF THE INVENTION

The purpose of this invention is to provide a device and system for placing unit doses of medication into a portable container labeled with textual and electronic information. The electronic information or electronic labeling is recorded on an information device. The information device is used in conjunction with other electronic devices to record when the doses of medication are given to a patient, the patient who received the medication, and the healthcare worker, such as a nurse, who administered the medication. The information device can include a sensor for sensing when the container is opened, a date and time clock for determining the time the medication is administered, and a locking mechanism. The locking mechanism locks the medication in the container until an appropriate time has been reached and the appropriate patient has been identified. The electronic labeling can include information regarding the intended patient, the names and quantities of each medication in the container, the time the medication is intended to be given, the physician who ordered the medication, the healthcare worker who dispenses the medication, and other pertinent information.

The information device may be separate from the portable container, and therefore not in contact with the medication, or it can be in integral part of the portable container. The information device includes a computer processor, a memory element, a power source and a communication device for transmitting and receiving electronic information to and from other electronic devices. The information device can also include a display, such as an LCD.

The information device is used in conjunction with an automated dispensing system that automatically dispenses desired medications into the portable container, or an automated dispensing system where a healthcare worker manually dispenses medication into the portable container. When medication is dispensed by an automated dispensing machine, the healthcare worker must properly identify themselves. This can be accomplished by the entry of a password unique to the healthcare worker. The healthcare worker then identifies the patient to whom medication is to be given. This may be by selection from a list of patients to whom the healthcare worker has been assigned. The healthcare worker may not select an inappropriate patient or one not in this area of the hospital. If the patient has been transferred outside of the area where the dispenser is located, the dispensing system can alert the nurse to this fact and can prevent any medication from being dispensed. The correct location of the patient may be determined via an information exchange with other computer systems in the hospital, e.g. Admit, Transfer, Discharge System (ADT) using a computer network, or this data can be maintained within the dispenser itself and updated manually.

Having selected a patient, the healthcare worker is presented with a list of medications that have been prescribed for the patient. Medication that can be given at this time, determined by the prescription regimen and the times of previous doses being consumed by the patient, may be distinctly displayed for selection. After selecting one or more medications and the quantity to give, the system dispenses each medication.

As each medication is dispensed, they are placed in the portable container. When all the desired medications have been dispensed, the container is closed, a textual label is written on the container with information to identify the patient, the medication, its quantity, when the medication is to be given, and other data as appropriate. The same information is also written electronically to an information device. After being written, the data is verified and attached to the container. The information device includes the medication information described above. Finally, the information device is attached to or otherwise associated with the portable container and presented to the healthcare worker. The information device can be attached to the container so that it locks the medication in the container until an appropriate clearance is granted, or the device can be constructed so that it only detects the opening of the container and communicates any necessary warning to the healthcare worker.

The medication may also be manually dispensed at a workstation from bulk containers into the portable container. The workstation includes a computer and input terminal to enter data, such as medication information regarding the medication placed in the portable container. The healthcare worker then uses the workstation to transmit or write the medication information to the information device. Alternately, the healthcare worker may use a computer workstation to determine the medications due to be given to the patient. By selecting the medication due to be given, the healthcare worker can cause the workstation to automatically prepare medication information for transfer to the information device.

The medication container may be of a single use variety, in which case only the information device is returned to the dispensing system for reuse. When the information device is returned to the dispensing system or presented to a computer workstation, the information device is read to assist in data recording and examined for any errors or operational problems. When the device is read, a variety of data may be retrieved from the information device besides that previously written to it regarding the medication information. This data may include the date and time the container was opened, information confirming that patient identification verification was used to confirm that the medication was given to the correct patient, and the healthcare worker identification of the person who gave the medication to the patient.

The medication information and other data is transmitted to the dispensing machine or the workstation in a format that can automatically be sent to the correct data base for the patients records and formatted appropriately for the data base system. An example of this is the creation of a Universal Record Locator (URL) address compatible with a hospital Intranet network. The address may be in a format not normally known to the dispensing system. Thus, the dispensing system can be used in several different hospitals without having to be significantly modified to accommodate differing address schemes. A medication report can also be formatted in a manner compatible with the Hypertext Markup Language (HTML), which will help preserve the independence of the dispensing system from the specific software requirements of the nurse reporting and charting system, which may vary from hospital to hospital.

In the case of any errors or operational problems being detected (e.g. inability to read the information stored in the information device, or battery beyond its expected service life), the device will be removed from service and stored in an area for retrieval by a service technician. A failure or service request message can be presented to the healthcare worker or sent by computer network to the pharmacy or hospital engineering department.

The information device will be compatible with a patient identification verification system. Such a system can transmit some or all of the patient identification information to the information device. This may be done by a communication between a patient information device, with a compatible communication device, attached to or associated with the patient and the information device. It may also be done by communication from a patient information device to a computer processor associated with a healthcare worker with a compatible communication device. The patient identification information is then communicated to the information device. The healthcare worker computer processor may be a workstation the worker has logged into, a portable computer device (e.g. personal digital assistant—PDA), or a healthcare worker information device such as an electronic badge that is worn. The healthcare worker computer processor is in some manner known to be temporarily or permanently associated with the patient, for example by having recently read the patient information device. In this case the medication information held in the information device can be transmitted to the healthcare worker computer processor and in turn can later be transferred to the dispenser or a computer workstation for prompt and automatic data recording or for transmission to database computer system as described above.

Other aspects and advantages of the invention will become apparent upon making reference to the specification, claims and drawings.

BRIEF DESCRIPTION OF THE DRAWINGS

FIG. 7 is a perspective view of an information device attached to a securing device that is secured to a fluid bag for holding IV or blood solutions, the securing device being in a locked position to prevent access to the IV solution via a nipple or tip of the fluid bag.

FIG. 8 is an elevated sectional view of an information device and securing device in its locked position.

FIG. 9 is an elevated sectional view of a securing device in an open position to allow access to the nipple or tip of the fluid bag.

FIG. 17 is a listing of the memory contents of the information device.

FIG. 18 is a listing of patient medication information.

FIG. 19 is a listing of dispensed medication information.

FIG. 20 is a listing of the memory contents of the patient information device.

FIG. 21 is a listing of the memory contents of the healthcare worker identification device.

FIG. 22 is a listing of the memory contents of a patient room workstation or computer peripheral device.

FIG. 23 is a listing of final medication transaction report.

FIG. 26 is a medication report for transmission in an HTML format.

FIG. 27 is a universal resource locator data storage address.

FIG. 28 is a medication report as displayed on a computer monitor.

FIGS. 29A and 29B is a flow chart showing the steps in verifying that medication is administered to the specific patient for whom the medication was prescribed as in a patient verification system.

FIGS. 31A and 31B is a flow chart showing the steps in recording which healthcare worker opens a medication container as in a medication tracking system.

DESCRIPTION OF THE PREFERRED EMBODIMENTS

While this invention is susceptible of embodiment in many different forms, the drawings show and the specification describes in detail a preferred embodiment of the invention. It should be understood that the drawings and specification are to be considered an exemplification of the principles of the invention. They are not intended to limit the broad aspects of the invention to the embodiment illustrated.

Information Device and Portable Container

Figure 1:
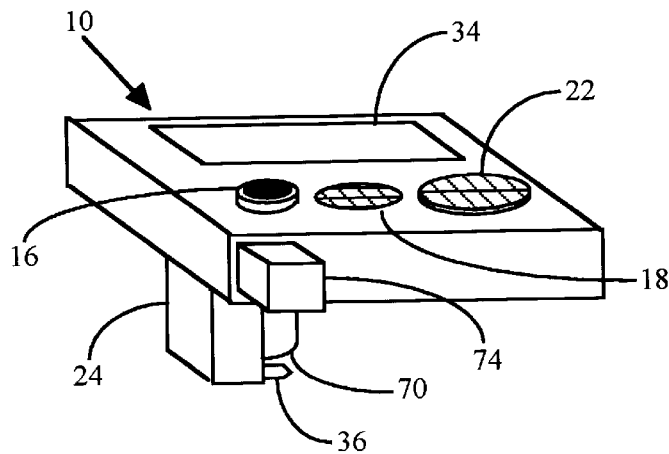
FIG. 1 is a perspective view of an information device having a latch for locking a portable container into a closed position.
Figure 2:
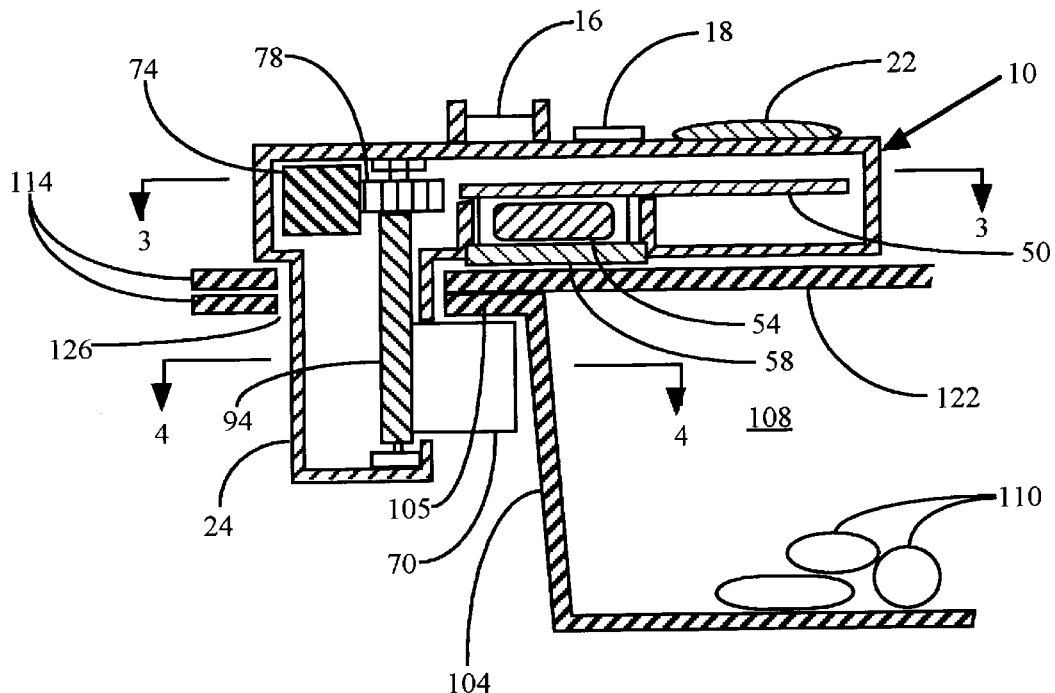
FIG. 2 is a sectional view of the information device attached to the container, with the latch of the information device locking the container into its closed position.

An information device 10 is shown in FIGS. 1–4. The information device 10 includes activation button 16, audible alert device 18, infrared receiver and transmitter or transceiver device 22, alignment projection 24 with securing latch 70, and latch release button 74. Securing latch 70 is movable between a locked position 71 and an unlocked position 72. The information device 10 also includes an optional display device or visual display 34 which may be an LCD device, and optional sensing switch 36. While the infrared transceiver 22 is shown and infrared communications described, it should be understood that many other methods of communication can be used, such as radio frequency communication, magnetic induction, direct electrical contact, ultrasound and the reading of bar codes. As best shown in FIG. 2, the internal components of the information device 10 include a processor 50, power source or battery 54, battery cover 58, and latch movement gear 78. It should be understood that the power source 54 may be a solar energy device, or it may be an external device providing energy by magnetic coupling or radio frequency transmission.

Figure 5:
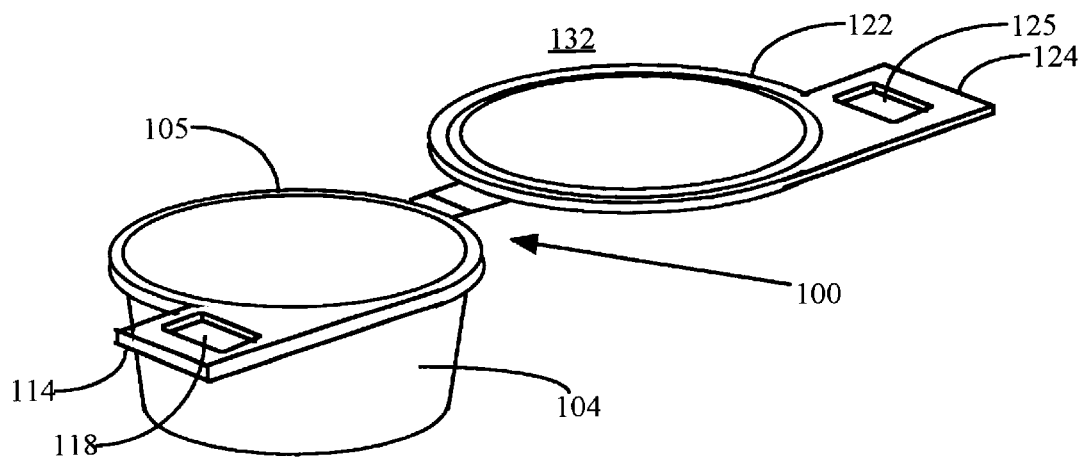
FIG. 5 is a perspective view of a portable medication container in an open position.
Figure 6:
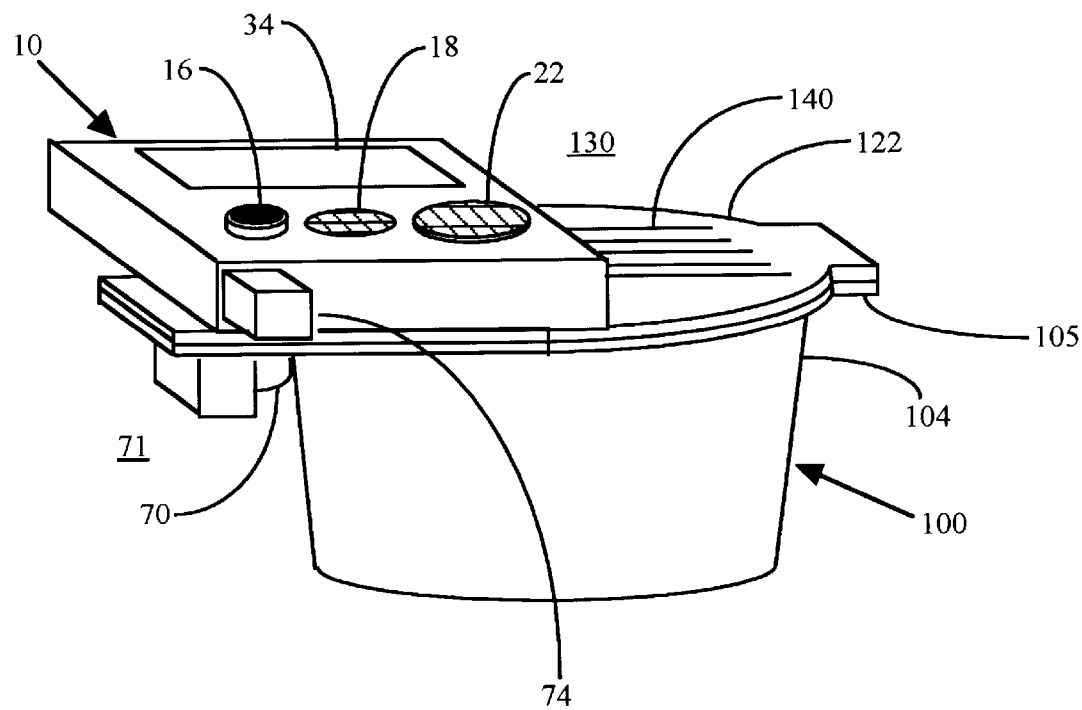
FIG. 6 is a perspective view of the portable medication container with the information device attached thereto and locking the container into its closed position.

A portable container 100 is shown in FIGS. 2, 5 and 6. The portable container 100 includes base 104 forming compartment 108 for holding the prescribed dose of medication 110. The base 104 has a rim 105 that forms an open top. One side of the rim 105 has an integral, projecting tab 114 with a hole 118 formed through its middle portion. The container 100 includes container lid 122 that is hingably attached to the other side of the rim 105. Lid 122 also has an integral, projecting tab 124 with a hole 125 formed through its middle portion. As shown in FIGS. 2 and 6, the hole 118 in the tab of the rim 114 is adapted to align with the hole 125 in the tab of the lid 124 when the lid is in a closed position 130. The holes 118 and 125 combine to form an opening 126 when in this closed position 130. The information device 10 is adapted to attach to the portable container 100 when the lid is in its closed position 130. The alignment projection 24 of the information device 10 passes through the opening 126 and combines with the forward extension of the securing latch 70 to prevent base 104 and lid 122 from separating and moving to an open position 132.

Figure 3A:
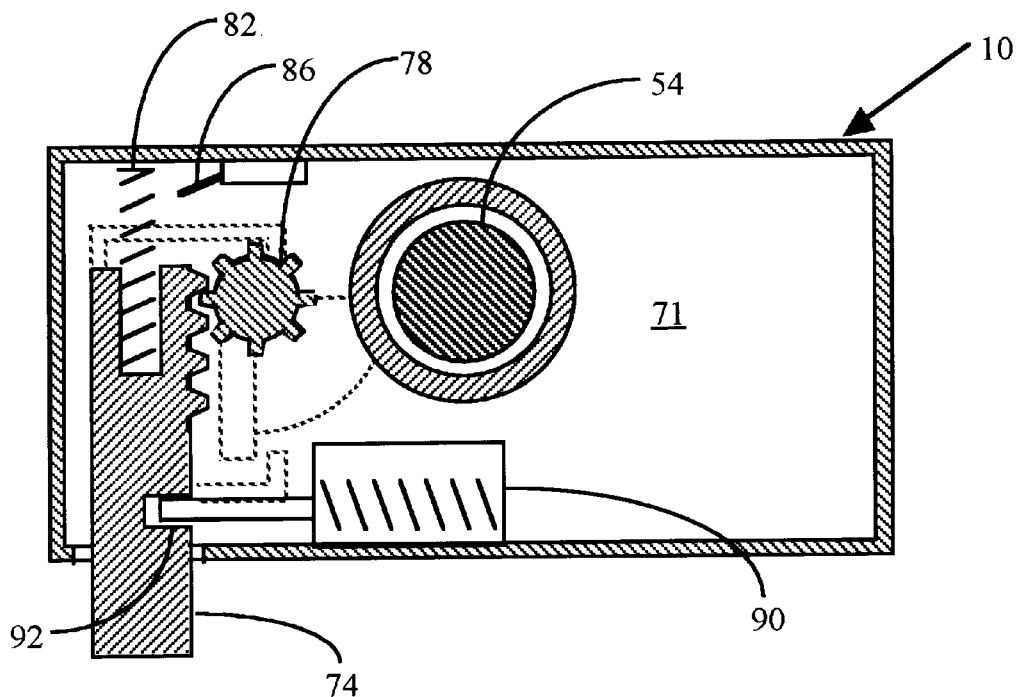
FIG. 3A is a sectional view of FIG. 2 taken along line 3—3 showing the locking mechanism of the information device with its latch in a locked position.
Figure 4A:
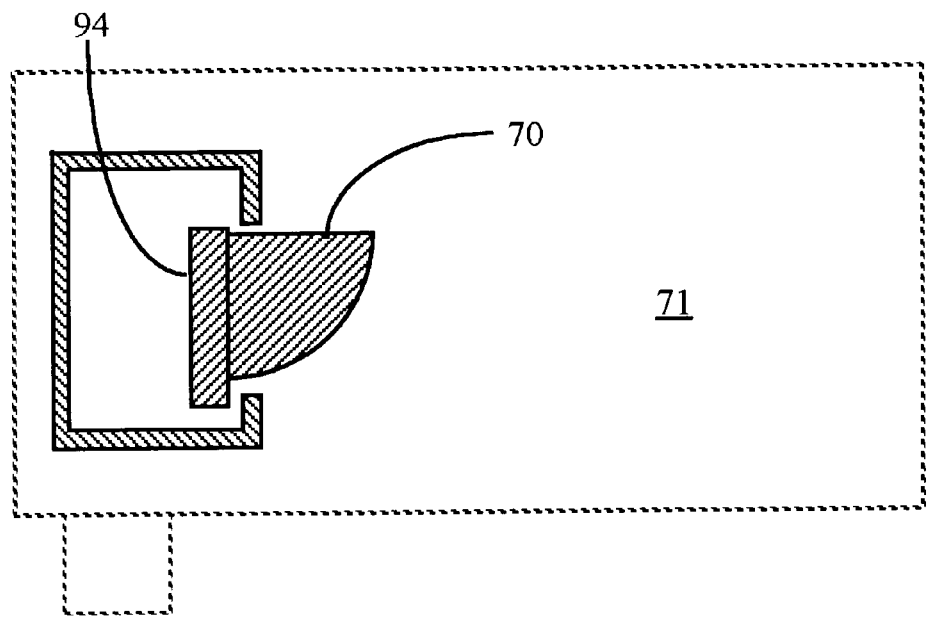
FIG. 4A is a sectional view of FIG. 2 taken along line 4—4 showing the locking mechanism of the information device with its latch in its locked position.

FIGS. 3A and 4A the securing latch 70 is in its locked position 71. Latch release spring 82 biases latch release button 74 into its extended position. An electric switch 86 is used to sense the motion of the button 74. An optional latch release solenoid 90 and the geared rack engage latch movement gear 78. A movable rod of latch release solenoid 90 is biased to extend into slot 92 to prevent the latch release button 74 from moving. The latch 70 includes a backing door 94 to keep foreign material out of the information device 10.

Figure 3B:
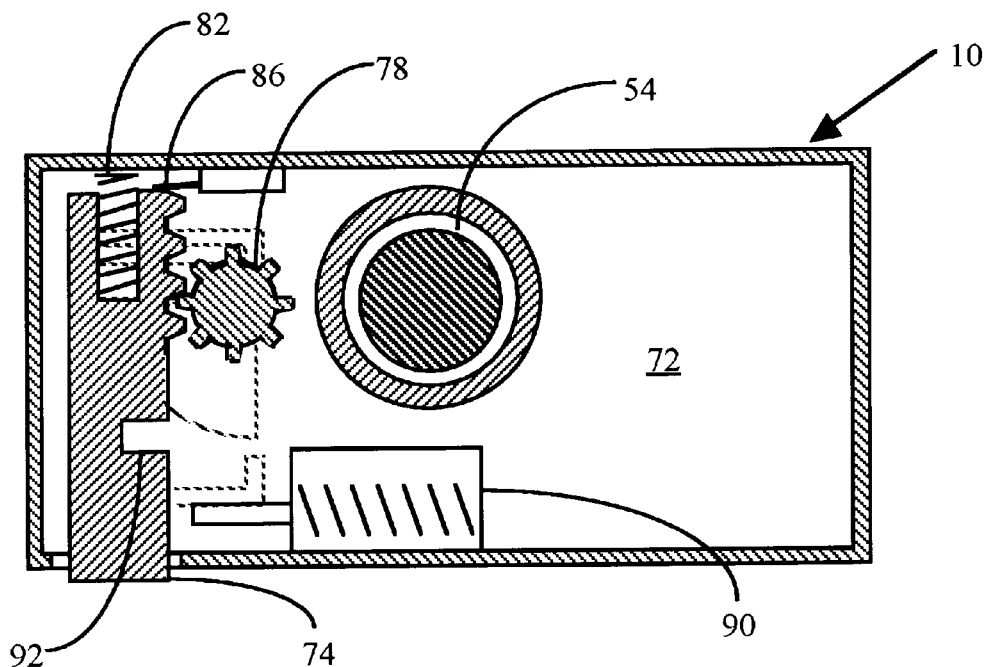
FIG. 3B is a sectional view of FIG. 2 taken along line 3—3 showing the locking mechanism of the information device with its latch in an unlocked position.
Figure 4B:
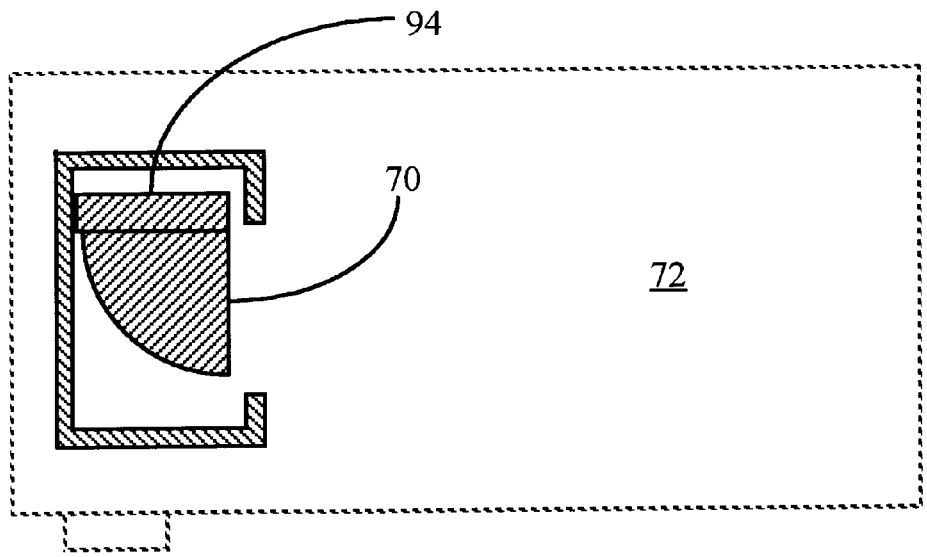
FIG. 4B is a sectional view of FIG. 2 taken along line 4—4 showing the locking mechanism of the information device with its latch in its unlocked position.

FIGS. 3B and 4B show the securing latch 70 is in its unlocked position 72. Securing latch 70 moves into unlocked position 72 when processor 50 receives appropriate instructions via transceiver device 22 to retract latch release solenoid 90. With the movement rod of the solenoid 90 retracted, latch release button 74 can be depressed to cause latch movement gear 78 to rotate and allow securing latch 70 to swing away from the locked position 71. Electric switch 86 is closed which indicates the button 74 was pressed. When the latch release button 74 is released, spring 82 will again bias the latch release button into its extended position. When the solenoid 90 is deactivated its movement rod will again extend into slot 92, securing latch 70 into its locked position 71.

FIG. 5 shows the portable container 100 in its closed position 130. Container 100 may be a disposable container intended for a single use to prevent medication cross contamination. The lid 122 includes a paper label 140 for printing textual labeling information as shown in FIG. 6. Alignment projection 24 can pass through the opening 126 so that the information device 10 can be removed, when securing latch 70 is retracted into its unlocked position 72, but not when the securing latch is extended into its locked position 71. FIG. 6 shows information device 10 secured to container 100 in its closed position 130. The latch 70 is in its locked position so that the container 100 cannot be opened. The doses of medication are locked inside the closed container 100. The display device 34 is provided to display a desired portion of the information contained in memory contents 500 of the information device 10. See FIG. 17, as discussed below.

FIGS. 7 to 9 show the information device 10 used in conjunction with a fluid bag securing device 150 and a fluid bag 170. The information device 10 assists in the electronic labeling of fluid bag 170 containing IV solutions or blood. Securing device 150 is an integral piece of plastic with first and second clamping portions 151 and 152 with upper surfaces 153 and 154. The clamping portions are joined by a living hinge 158 located proximal the upper surfaces. Each clamping portion has a recess 162 and a pressure ridge 166. As shown in FIG. 8, the hinge 158 enables the clamping portions to fold so the recesses 162 and pressure ridges 166 can tightly surround an extended tip 172 of fluid bag 170 preventing flow or normal use of the fluid bag 170. When securing device 150 is folded, holes 167 and 168 form opening 169 allowing alignment projection 24 to pass through when securing latch 70 is retracted, but not when it is extended. FIG. 7 and 8 show the securing device 150 in closed position 130 surrounding and securing fluid bag tip 172 with the information device 10 attached in locked position 71.

Figure 10:
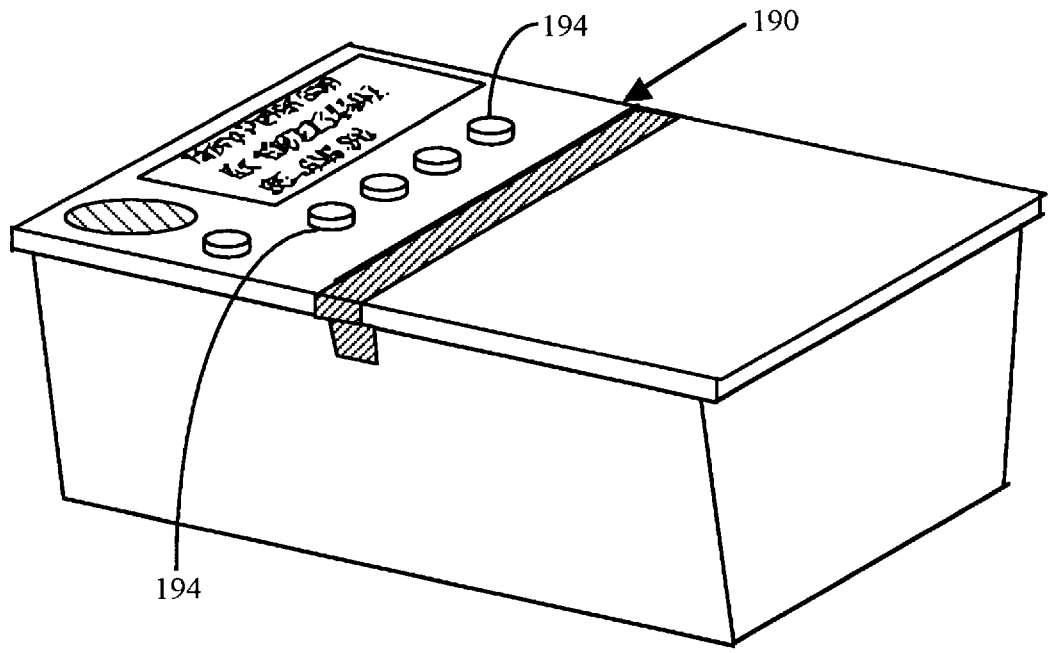
FIG. 10 is a perspective view of an integral portable container and information device with the information device built into its cover.

FIG. 10 shows an integral portable container and information device 190 which may be used for IV bags 170, syringes, body tissues, body organs or other larger objects. The information device 10 is an integral part of the covering lid. Optional data entry buttons 194 are provided to enter data or modify information about medication given to a patient. It should be understood that data entry buttons 194 could also be provided on information device 10.

Figure 11:
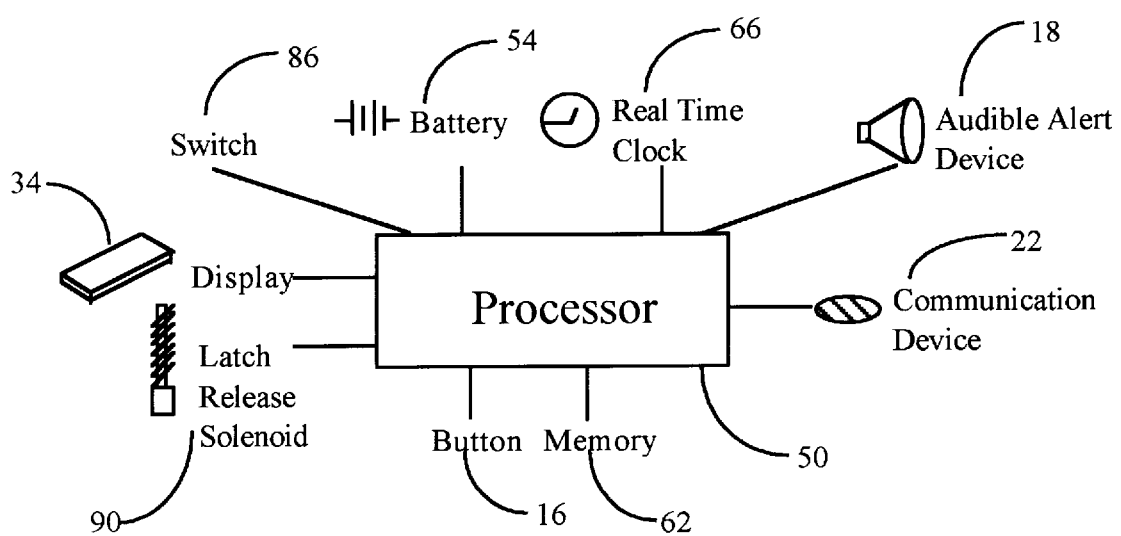
FIG. 11 is a schematic drawing of the electronic circuitry for the information device.

FIG. 11 is a schematic circuit diagram for information device 10 or the information device portion of integral container 190. The information device 10 includes computer processor 50, memory element 62, and real time clock 66 as well as controls to interact with activation button 16, latch release solenoid 90, optional display device 34, battery 54, audible alert device 18 and communication device 22.

FIG. 17 shows a list of memory contents 500 maintained in the memory element 62 of the information device 10. The memory contents 500 includes information specific to the information device 10, such as information device data elements 504 which contain a serial number 505, end of battery life data 506, and communication encryption codes 507.

The memory contents 500 includes information received from other electronic devices, such as the automated or manual dispensing systems 200 or 280 as discussed below. Information received from dispensing systems 200 or 280 can include selected predetermined patient information 520, selected prescribed medication dose information 540, predetermined healthcare worker information 560, dispensed medication information 580, medication information 581 and medication report components 600. Memory contents 500 can further include specific patient information 621 received from a patient identification device 300, a healthcare worker identification device 320, or a patient room information workstation 350 or computer peripheral device 355. Memory contents 500 can include administering healthcare worker information 681 received from the healthcare worker identification device 320.

Memory contents 500 can include consumption information 640 generated during use. Consumption information 640 can include consumption time information (e.g., consumption date and time information) 642 regarding when the portable container was opened 642, offered medication amount information 643 regarding the amount of medication offered to a specific patient 360, and consumed medication amount information 644 regarding the actual amount of medication consumed by the specific patient 360. Memory contents 500 can include a final medication transaction report 660. It should be understood that the memory contents 500 may include additional elements or fewer than shown in FIG. 17. Each of these sources of information and the use of the various information elements 500 can vary based on the intended use of information device 10 such as in a patient verification system, healthcare worker authorization system, medication tracking system, etc. as more fully described below.

Automated Dispensing System

Figure 12:
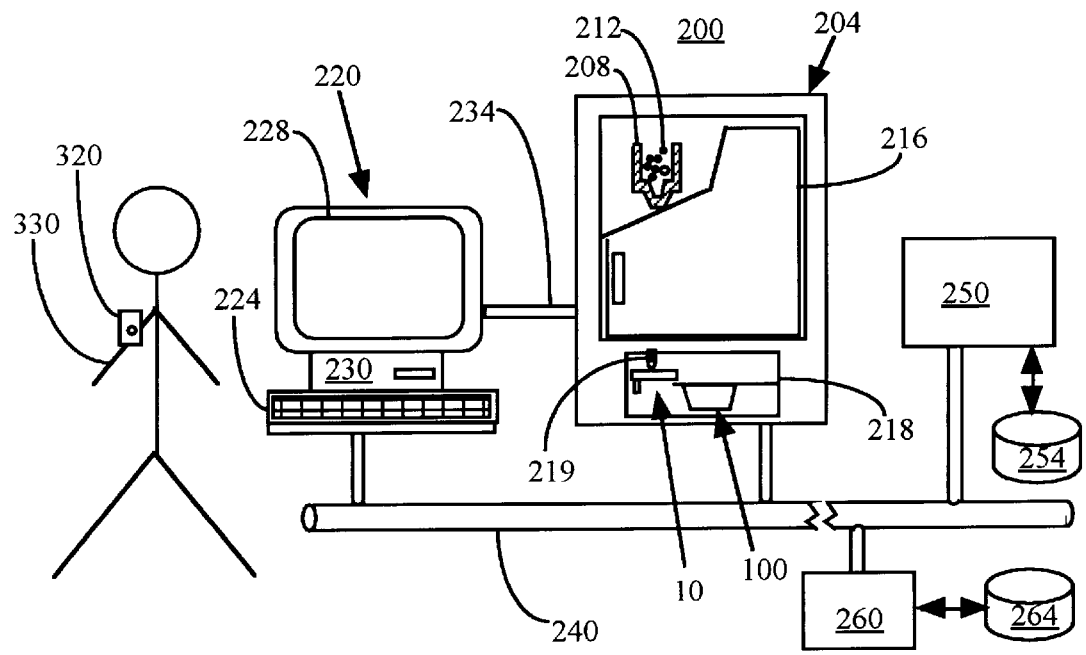
FIG. 12 is a plan view of a healthcare worker using an automated dispensing system that includes a dispensing machine and a medication dispensing workstation, both connected via a hospital network to a pharmacy database and a hospital database.

FIG. 12 shows the automated dispensing system 200 including an automated dispensing machine or unit dose dispenser 204 containing a plurality of bulk medication containers 208 stored inside the dispenser. Each bulk container 208 contains a specific type of medication 212. An access door 216 to the bulk containers 208 is kept locked. Access to the containers 208 is limited to authorized personnel in charge of maintaining the inventory of medication 212 in the dispenser 204, such as the hospital pharmacist. The dispensing machine 204 also contains an access port 218 through which the filled and sealed portable containers 100 are dispensed. A transceiver device 219 is provided for communicating information to the information device 10. Dispenser 204 is used in conjunction with a dispensing workstation 220.

The dispensing workstation 220 includes an input terminal 224 such as a keyboard or a pointer device, and a monitor 228 for communicating with the dispensing machine 204. The workstation 220 also includes a computer processor 230 and program software for controlling the operation of the dispenser 204 and the flow of information and instructions to and from the dispenser. The dispenser 204 or workstation 220 can communicate by a direct communication line 234 or via a hospital network 240. However, it should be understood that the computer processor 230 or an alternate computer processor could be located directly inside the dispenser 204 or included as a part of a hospital network 240.

The hospital network 240 can include its own internal database or can be connected to a pharmacy system 250 with pharmacy database 254 or a hospital information system 260 with a hospital database 264. The internal database or the workstation, or the separate databases 254 and 264 of the pharmacy and hospital systems 250 and 260, contains information pertaining to a plurality of physician orders such as prescription regimens or prescribed medication dose information 540 for administering medication 212 to a plurality of predetermined patients listed at least one of the databases. The databases includes predetermined patient information 520 and corresponding prescribed medication dose information 540 for each patient in the database. The computer processor 230 of the workstation 220 communicates with and obtains information from and relays information to its internal database, pharmacy database 254 or hospital database 264.

A healthcare worker 330 uses the automated dispensing system 200 to obtain prescribed doses of medication 110 for a specific patient 360 under his or her care. Before the dispensing machine 204 dispenses medication 110, the workstation 220 requests the healthcare worker 330 to select one of the predetermined patient in the database. The selected predetermined patient or selected patient should correspond to the specific patient 360 under his or her care. The healthcare worker 330 dispenses the prescribed dose or doses of medication by entering some form of selected patient information 520 that corresponds to the selected patient listed in the database. Alternatively, the healthcare worker 330 can select the name of the desired predetermined patient from a list of predetermined patients in the workstations internal database or by using the hospital information system 260 to locate the desired predetermined patient from the hospital information database 264. The list of predetermined patients to choose from may be limited to those who have been assigned to healthcare worker 330. Having identified the selected patient from the database 262 that corresponds to the specific patient 360 under his or her care, dispensing workstation 220 locates patient medication information 700 (See FIG. 18) for the selected patient in the workstations internal database or by using pharmacy system 250 to locate the information in pharmacy database 254.

Patient medication information 700 contained in the workstation database or associated databases 254 or 264 includes predetermined patient information 520 and corresponding prescribed medication dose information 540 for each predetermined patient. The physician prescription orders determine what prescribed medications correspond to which patient. The database also includes predetermined healthcare worker information 560 that is associated with the prescribed medication dose information. The prescribed medication dose information includes information designating what title or level of authority or clearance an authorized healthcare worker must have to administer the medication to a patient. Predetermined patient information 520 can include patient identification number 521, patient name 522, admitting physician 523, and patient room number, 524, and patient blood type 525. The predetermined patient information preferably includes at least patient identification number 521.

Figure 24:
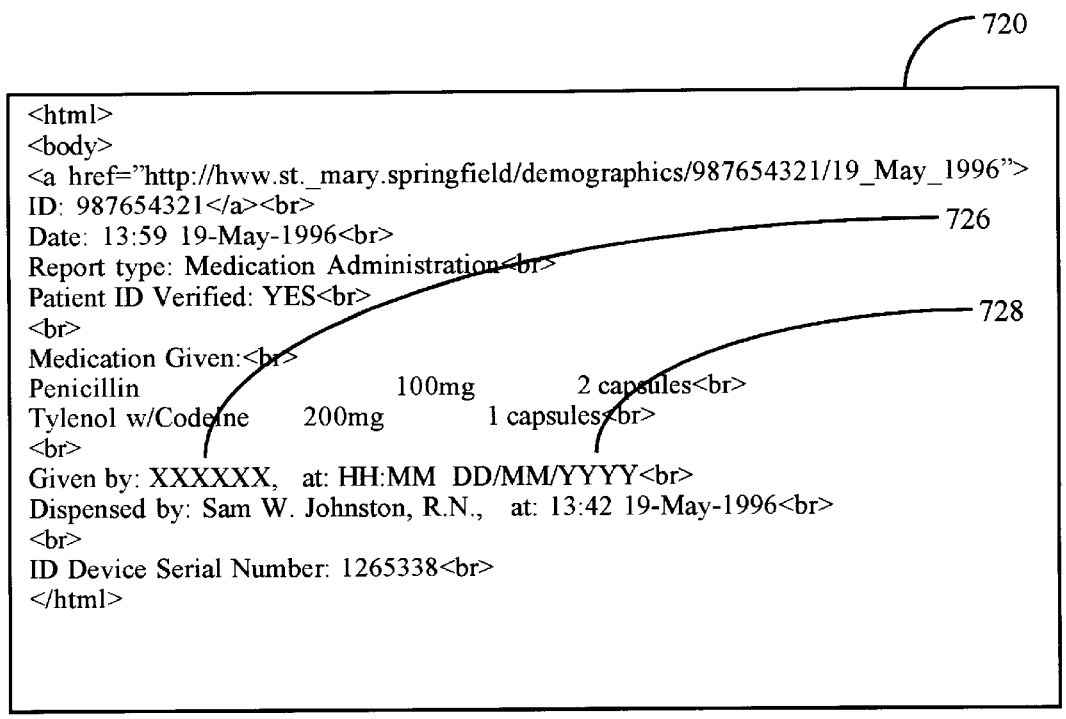
FIG. 24 is a medication report for transmission in an HTML format.
Figure 25:
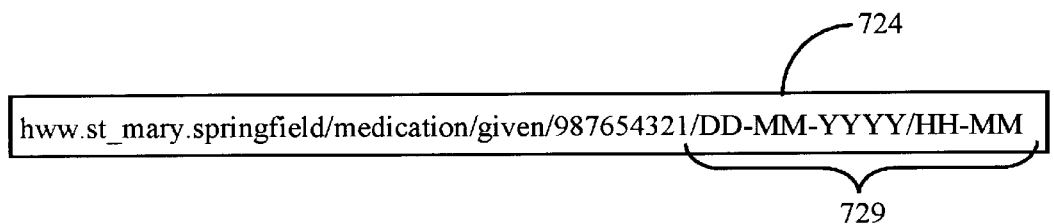
FIG. 25 is a universal resource locator data storage address.

Prescribed medication dose information 540 for each prescribed dose of medication 110 can include medication type 541, medication quantity prescribed 542, dosing times 543, and identification of physician prescribing medication 544. Patient medication information 700 can include medication report 720, FIG. 24, and universal resource locator 724, FIG. 25 which are reformatted by information device 10 as described infra. Predetermined healthcare worker information 560 can include the responsibilities, title or level of authority of the healthcare worker 561 allowed to give the prescribed medication, healthcare worker identification number(s) 562 allowed to give the prescribed medication, healthcare worker names(s) 563 allowed to give the prescribed medication, and list of patients 564 under care of each healthcare worker. Predetermined healthcare worker information preferably includes the responsibilities, title or level of authority of the healthcare worker 561.

The computer processor 230 and monitor 228 present prescribed medication dose information 540 for the medications that have been prescribed for the selected patient. The healthcare worker 330 then selects the medication to dispense from this list. Healthcare worker 330 can also enter a medication to be dispensed without the aid of the list or not on the list. In either case, computer processor 230 determines whether the medication is stocked in any of the holding containers 208. If not, an error message will be presented or displayed on the monitor 228. If the medication is available, computer processor 230 causes the dispenser 204 to dispense individual doses of the selected medication 110. As each dose of medication 110 is dispensed, they are placed in the compartment 108 of portable container 100. When all the doses of medication 11O have been dispensed, the lid 122 of the container 100 is closed by dispenser 204 to preventing access to medication.

As medication 212 in the bulk container 208 is dispensed for the selected patient, computer processor 230 creates dispensed medication information 580 for the doses of medication 110 dispensed. Dispensed medication information 580 can include medication information 581; date and time medication dispensed 582, identification of healthcare worker 583 who dispensed medication, and type and quantity actually dispensed 584. Dispensed medication information 580 can also include medication report components 600, medication report 720 and universal resource locator 724 whose use are discussed below.

When all the prescribed doses of medication 110 for the selected patient are dispensed into the portable container 100, selected portions of patient medication information 700 and dispensed medication information 580 are communicated to information device 10 by dispenser 204 using transceiver device 219 via a dispensing signal. This is shown in steps 800, 860, and 910 in FIGS. 29A, 30A, 31A. The transferred information is stored in the memory element 62 of the information device 10. The use of the selected portions of patient medication information 700 vary based on the intended use of information device 10 such as in a patient verification system, healthcare worker authorization system, medication tracking system, etc., as more fully described below.

Information device 10 may intermittently turn itself off to conserve power when stored in the dispenser during periods of non-use. The dispenser 204 can press activation button 16 to initiate the transfer of data. The data received by the information device 10 can be communicated back to the dispenser 204 as part of a verification process.

Once information device 10 receives the dispensing signal, computer processor 230 sends a message to the information device 10 to retract the latch release solenoid 90. The dispenser 204 automatically presses the latch release button 74 to cause securing latch 70 to swing to its unlocked position 72. This step may also be accomplished manually by healthcare worker prior to inserting the information device 10 into the dispenser 204. Latch release button 74 also makes contact with electric switch 86 which is sensed by processor 50 and causes latch release solenoid 90 to be biased to return to its extended position. Projection 24 of the information device 10 is now aligned with and moved along a path of travel so that the projection passes through the opening 126 formed by the base 104 and closed lid 122. The bottom surface of the information device 10 now rests on the upper surface of the lid 122 of the container 100. Latch release button 74 is then released to allow the spring 82 to force latch release button to move into its extended position 71, so that securing latch 70 rotates to its extended or locked position 71. The upper surface of the latch 70 now abuts the lower surface of the rim 105 of the container 100. Latch release solenoid 90 then enters slot 92, which prevents securing latch 70 from moving out of its locked position 71. The container 100 is now removed from dispenser 204 through access port 218. Access port 218 can be secured to prevent removal of container 100 until information device 10 has been secured and locked to the portable container 100.

When prescribed dose or doses of medication 110 are dispensed into portable container 100, the dosing times 543 or time ranges for when the medication is to be administered can be included with the dispensing signal transferred to information device 10. Dosing times 543 are used by processor 50 in conjunction with real time clock 66 to prevent latch release solenoid 90 from being retracted until the prescribed time or time range is reached. This feature helps prevent the healthcare worker 330 from administering the medication inside the container 100 to the specific patient 360 under his or her care too soon. Processor 50 can also use its audible alert device 18 to issue a reminder tone when the time or time range is reached. This tone is used to indicate to the healthcare worker 330 transporting the medication that it is time to administer doses of medication 110 to the predetermined patient.

Manual Dispensing System

Figure 13:
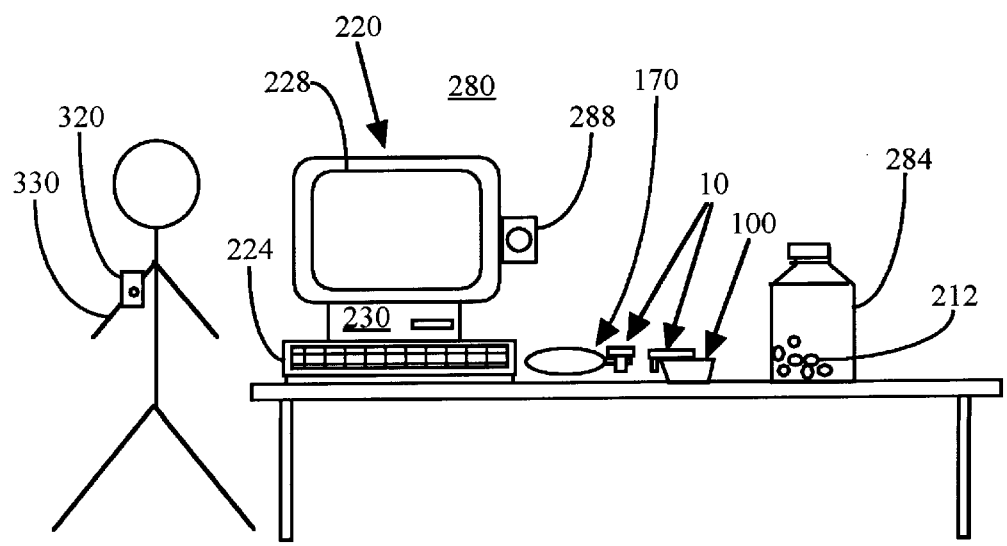
FIG. 13 is a plan view of a healthcare worker using a manual dispensing system with the healthcare worker using the dispensing workstation to manually dispensing medication and labeling medication containers.

FIG. 13 shows the manual dispensing system 280 which includes dispensing workstation 220. Healthcare worker 330 manually locates a bulk medication container 284 holding a quantity of a specific type of medication 212 for dispensing to a specific patient 360 under his or her care. Healthcare worker 330 then removes the prescribed dose or doses of medication 110 from container 284 and places these doses in compartment 108 of portable container 100, and closes lid 122. Healthcare worker 330 then uses workstation 220 to identify the medication and the amount of that medication that has been selected and placed in the container 100 for administering to the predetermined patient. Healthcare worker 330 may also use input terminal 224, to identify the medication selected for administering to the selected patient from patient medication information 700.

When all the prescribed doses of medication 110 for the selected patient are manually dispensed into portable container 100, selected portions of patient medication information 700 and dispensed medication information 580 are communicated to information device 10 via communication port 288 which transmits the initial dispensing signal to the information device 10 for storage in memory element 62. If the patient medication information 700 is not available, portions of selected patient information 520 and predetermined healthcare worker information 560, as entered by healthcare worker 330 using workstation 220, may be sent as part of the dispensing signal. This is shown as steps 800, 860, and 910 in FIGS. 29A, 30A, and 31A.

The healthcare worker 330 manually secures the information device 10 to the container 100. This is done by closing the lid 122 of the container, pressing latch release button 74, inserting the projection 24 of the information device into the opening 126 of the container. The bottom surface of the information device 10 now rests on the upper surface of the lid 122 of the container 100. The healthcare worker then releases latch release button 74 so that latch 70 is biased by spring 82 into its locked position 71. The upper surface of the latch 70 now abuts the lower surface of the rim 105 of the container 100. The information device 10 and portable container 100 are now in there closed and locked positions 130 and 71, which prevents the container from inappropriate opening.

The workstation 220 can also be used to aid in manually preparing a fluid bag 170 for administering to the predetermined patient as in FIG. 13. Various medications are prepared and mixed in fluid bag 170. Once the medication is mixed and the fluid bag is filled, securing device 154 is placed around the fluid bag tip 172 of the fluid bag. The information device 10 is then attached in locked position 71 to the securing device 154 to prevent the inappropriate use of the fluid bag 170.

Information device 10 contains portions of dispensed medication information 580 regarding each medication mixed in fluid bag 170. Dispensed medication information 580 can be written to information device 10 by workstation 220 as each medication is mixed as part of the dispensing signal. Workstation 220 is used to transfer portions of selected patient information 520 and predetermined healthcare worker information 560 to information device 10. This transfer of the selected patient identification information is done either at the time the medication is mixed in fluid bag 170 or before the fluid bag is transported to the patient to whom it is to be administered. In this manner, medication is premixed in fluid bag 170 and stored in a convenient location so that healthcare worker 330 has quick access to the premixed fluid bag, yet portions of predetermined patient information 520 can still be added to information device 10 prior to transportation to the specific patient 360.

Communication port 288 is used to read dispensed medication information 580 stored in the information device 10 previously attached to a fluid bag 170 containing premixed medication. Healthcare worker 330 then uses workstation 220 to communicate with pharmacy system 250 to verify that the medication in fluid bag 170 has been prescribed for the predetermined patient. The workstation 220 will inform the healthcare worker 330 if the medication in fluid bag 170 is prescribed for the selected patient and alert healthcare worker 330 if it is not. If it is intended for the selected patient, workstation 220 can transmit a supplemental signal containing the selected predetermined patient information 520 to information device 10.

Container 100 or fluid bag 170 with securing device 154 are now secured and locked in closed position 130 by information device 10, and are ready for transport to a specific patient 360 in a particular hospital room 380.

Patient Verification System

Figure 15:
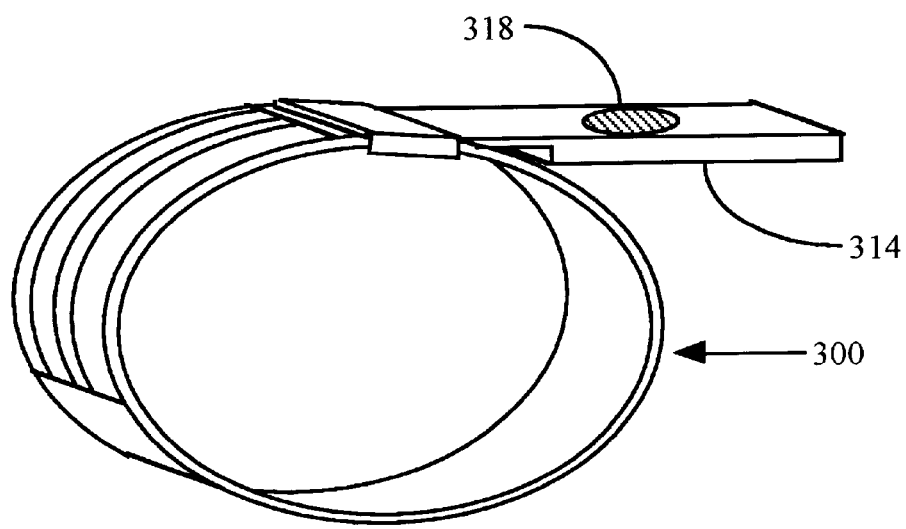
FIG. 15 is a perspective view of a patient identification device.
Figure 16:
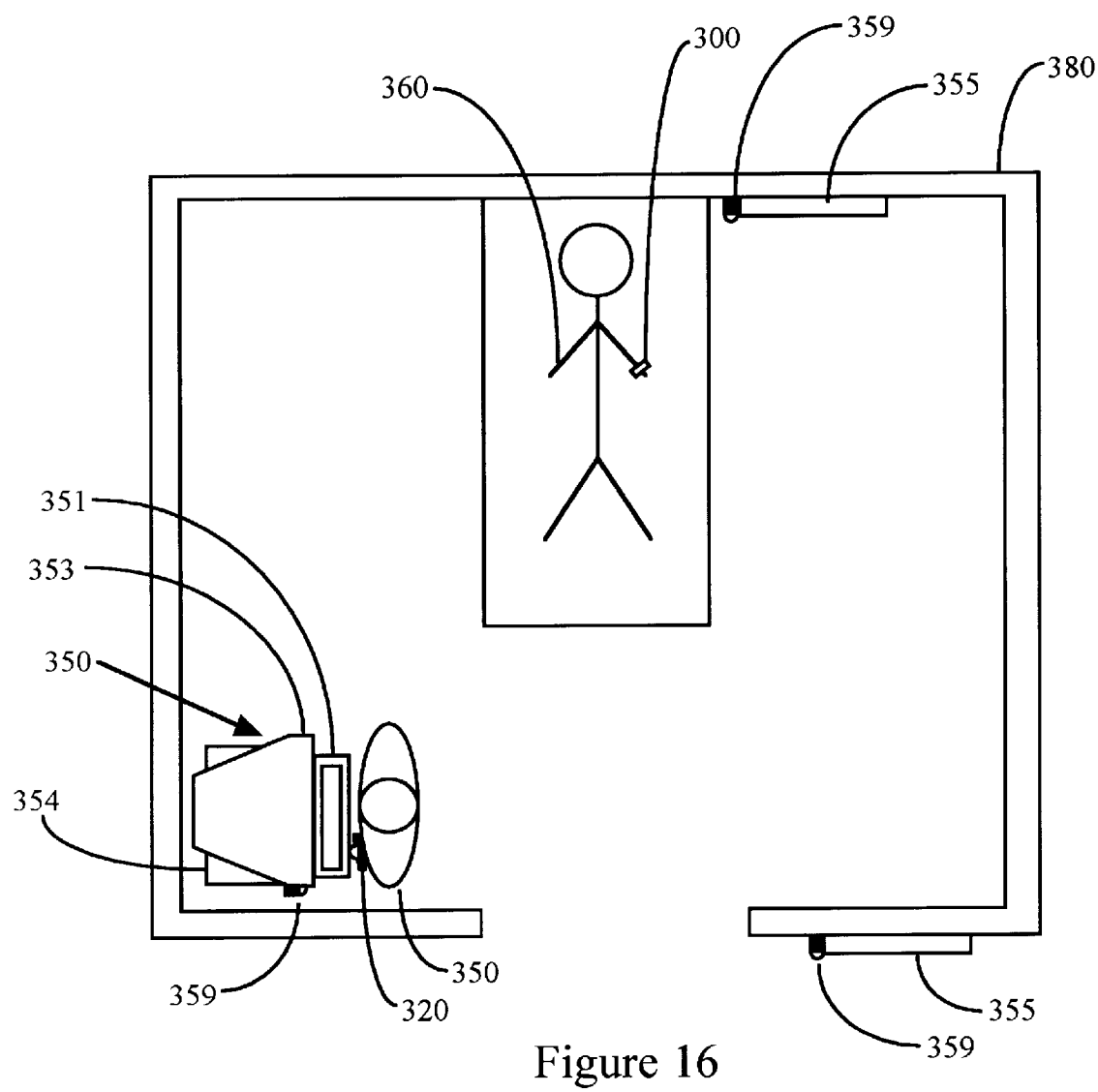
FIG. 16 is an overhead plan view of a hospital room with a specific patient in a bed and an administering healthcare worker at an information station containing a computer and electronic equipment.
Figure 29B:
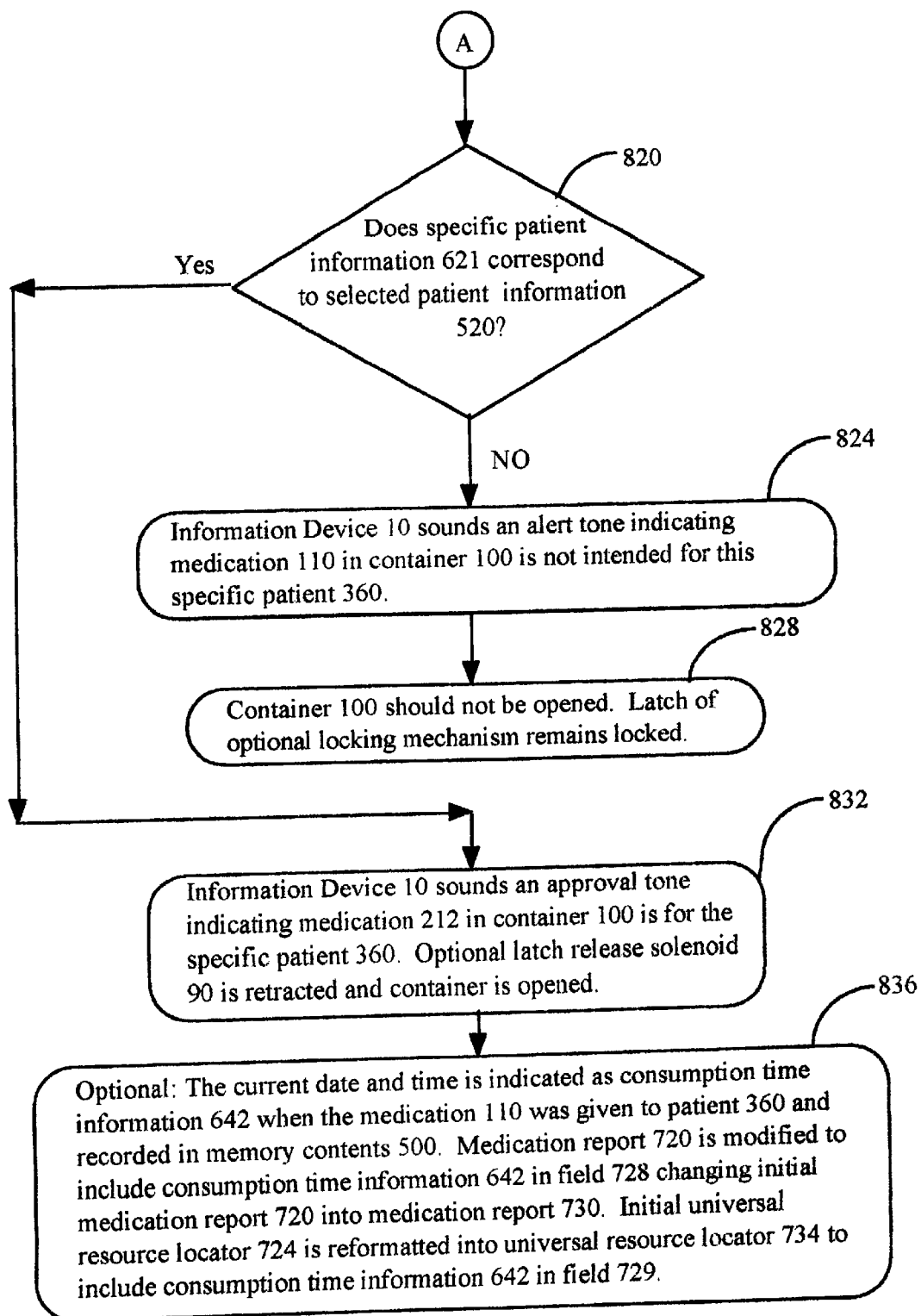

A patient verification system is accomplished by providing the specific patient 360 with patient identification device 300 as in FIGS. 15 and 16. Patient identification device 300 can take the form of a wrist bracelet. Patient identification device 300 has a processor 314 and a communicating device 318 that is compatible with the information device 10. Memory contents 620 is held in a memory of processor 314. FIG. 20 provides a list of information contained in the memory of the patient identification device 300. Memory contents 620 can include specific patient information 621, such as patient identification number 622, patient name 623, list of medications to which patient is allergic 624, admitting physician 625, and patient blood type 626. While specific patient information 621 is shown as a list of data, the list is may include additional data elements or fewer than shown. Preferably specific patient information 621 contains at least patient identification number 622. A flow chart showing a series of steps 800–836 for performing the patient verification system is shown in FIGS. 29A and 29B.

Communicating device 318 transmits specific patient information 621 for the specific patient 360 (step 800). When container 100 and attached information device 10 are brought near to patient identification device 300 (step 804), healthcare worker 330 presses activation button 16 (step 808). This causes information device 10 to transmit a signal that is received by the patient identification device 300. Patient identification device 300 responds by transmitting a verification signal containing the specific patient information 621 that is received by the information device 10 (step 812). The computer processor or comparison device 50 of the information device 10 compares portions of specific patient information 621 with corresponding elements of selected patient information 520 stored in the memory contents 500 of the information device (step 816). While the specific patient information 621 is stated to be transmitted to the information device 10 for comparison with the selected predetermined patient information 520, it should be understood that this information could be transmitted to a different comparison device such as a healthcare worker identification device 320, an information workstation 350 or a computer peripheral device 355 for comparison.

When specific patient information 621 corresponds to predetermined patient information 520 (step 820), information device 10 provides an approval tone using the audible alert device 18 to indicate that the prescribed dose of medication 110 in portable container 100 are intended for that specific patient 360 (step 832), and latch release solenoid 90 is activated to enable securing latch 70 to be released into unlocked position 72 by healthcare worker 330. Once released, the alignment projection 24 of the information device 10 is removed from opening 126 of container 100 so that the lid 122 can be moved to its open position 132. The term "corresponds to" means that the portion of information being compared matches, agrees with, falls within a range prescribed by, or correlates to the information to which it is being compared.

The real time clock 66 in the information device 10 is used to record consumption time information (e.g., date and time portable container opened information) 642 (step 836). This date and time information corresponds to when the medication 110 is given or administered to the specific patient 360. This consumption time information 642 is recorded in the memory element 62 of the information device 10 as part of consumption information 640. Medication report 720 and universal resource locator 724 are modified to include the date and time container opened information 642 in fields 728 and 729 to create a final medication report 730 as shown in FIG. 26, and the final universal resource locator 734 part of medication report components 670 as in FIG. 27.

When specific patient information 621 differs from or does not correspond to the selected patient information 520 an error tone is sounded by audible alert device 18 (step 824). Latch release solenoid 90 keeps securing latch 70 in its locked position 71 (step 828), so that the healthcare worker 330 cannot open the container 100 and give the medication to the wrong patient. The term "differs" means that the portion of information being compared does not match, agree with, fall within the range prescribed by, or correlate to the portion of information to which it is being compared.

As shown in FIG. 16, the patient verification system can be accomplished by placing a workstation 350 or computer peripheral device 355 in or near the room 380 of the specific patient 360. The workstation 350 or computer peripheral device 355 can broadcast specific patient information 621 using communication device 359 to the information device 10 on request. Workstation 350 includes input device 351, monitor 353, and processor 354. Workstation 350 or computer peripheral device 355 must be known by the healthcare worker 330 to be associated with specific patient 360 and has memory contents 690 including specific patient information 621 as in FIG. 22. This specific patient information 621 is transmitted to information device 10 as described above. The specific patient information 621 preferably includes patient identification number 622.

The patient verification system can also be accomplished by using healthcare worker identification device 320, described below, to receive specific patient information 621 from patient identification device 300, and in turn transmit this data to information device 10 to authorize the unlocking of container 100.

Healthcare Worker Authorization System

Figure 14:
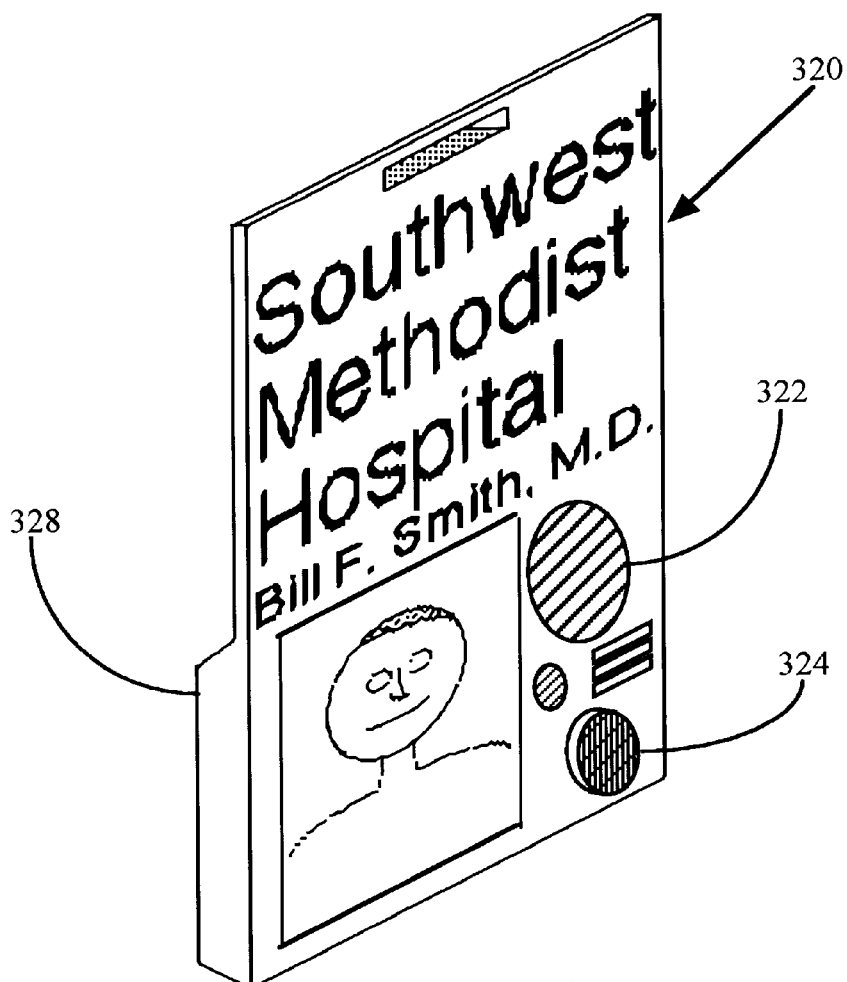
FIG. 14 is a perspective view of a healthcare worker identification device.
Figure 30A:
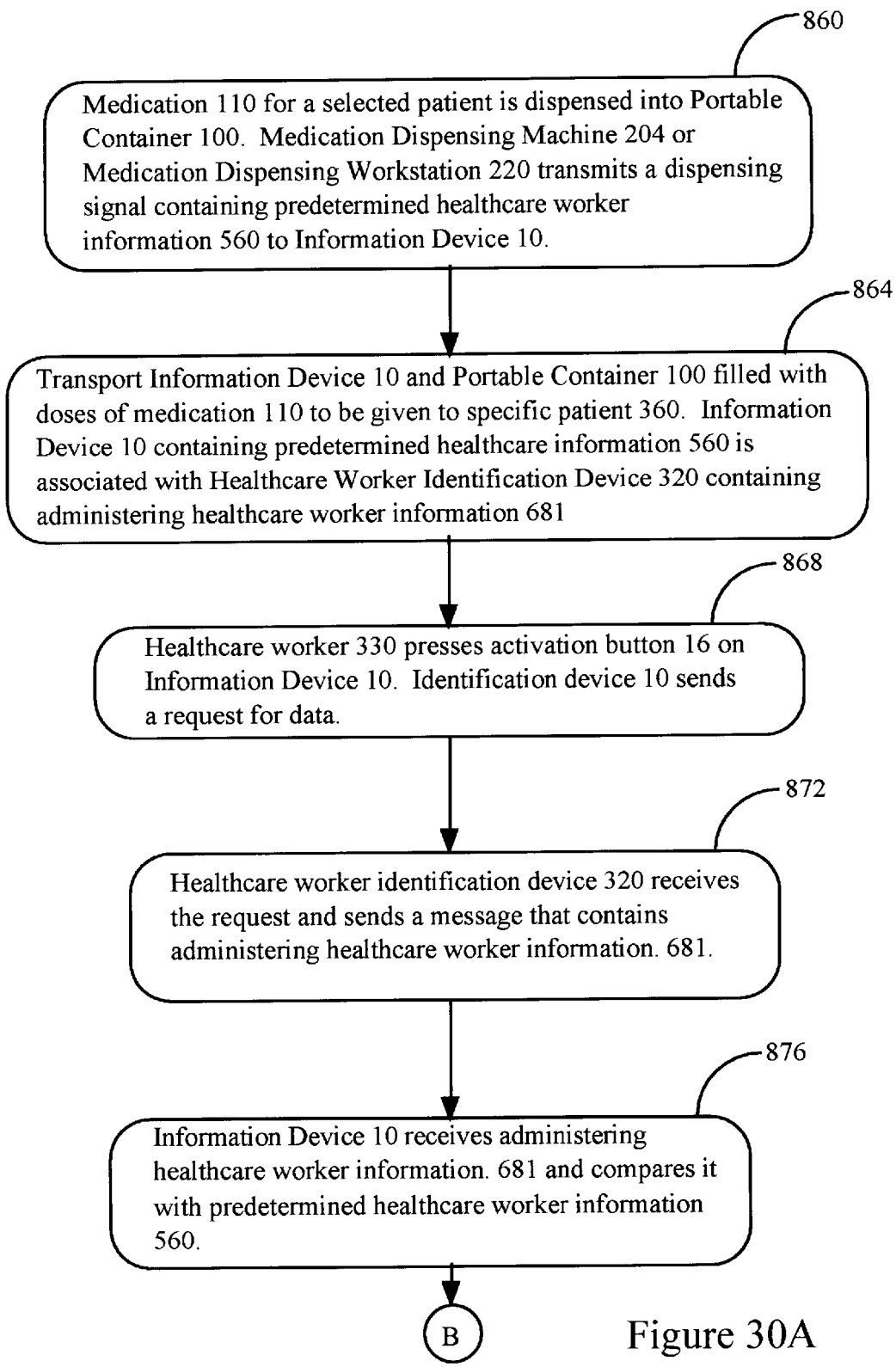
FIGS. 30A and 30B is a flow chart showing the steps in verifying that a specific healthcare worker is authorized to give medication as in a healthcare worker verification authorization system.
Figure 30B:
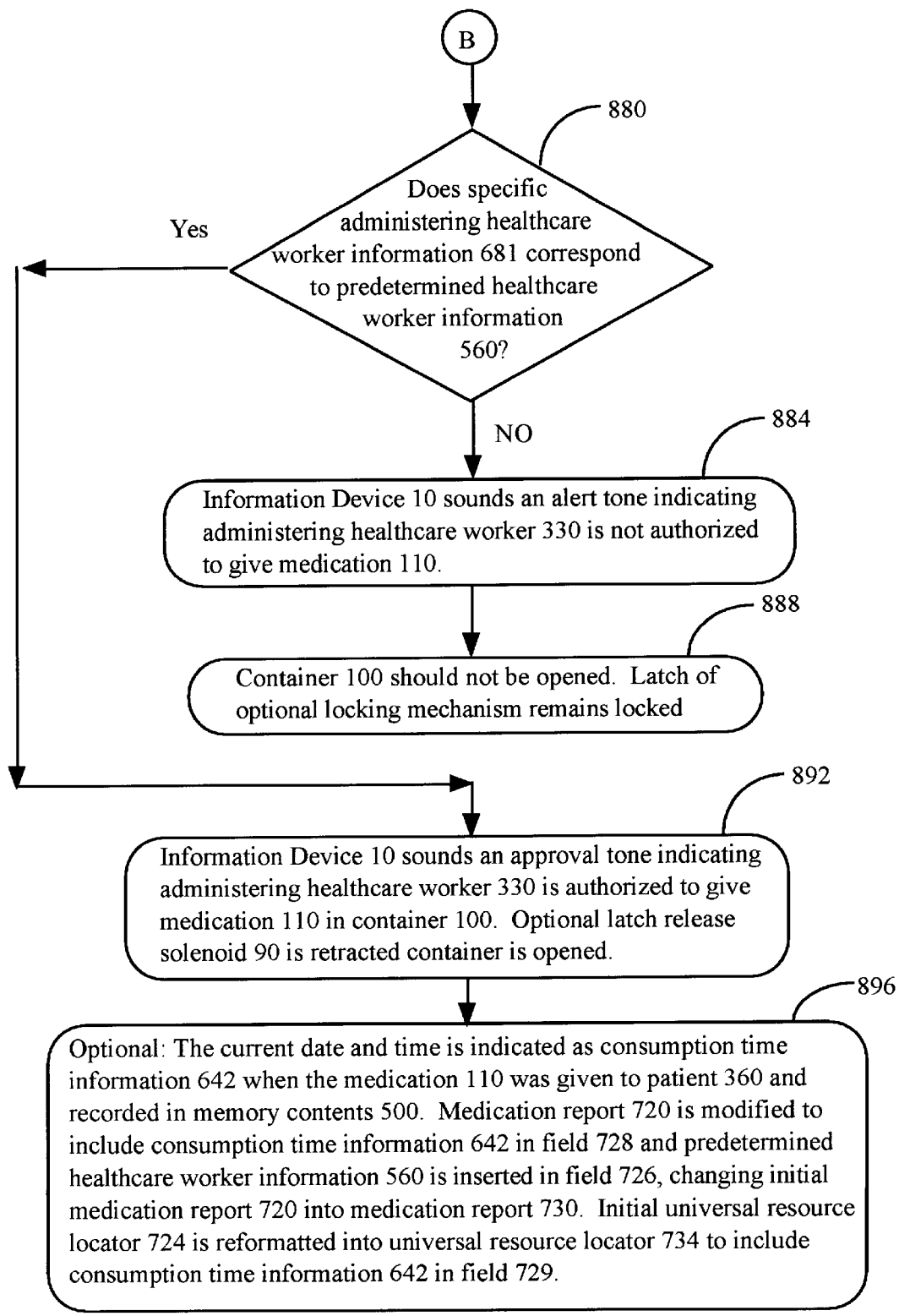

A healthcare worker authorization system can be accomplished by having healthcare worker 330 wear or carry healthcare worker identification device 320 that can communicate compatibly with information device 10. The healthcare worker identification device 320 may take the form of an identification badge as in FIG. 14. Healthcare worker identification device 320 has communication device 322, activation button 324, and processor and memory section 328. A flow chart showing a series of steps 860-896 for performing the healthcare worker authorization system is shown in FIGS. 30A and 30B.

As shown in FIG. 21, the memory contents 680 of the healthcare worker identification device 320 is held in memory of processor 328. Memory contents 680 can include administering healthcare worker information 681, such as responsibilities or title 682, identification number 683, name 684, list of patients 685 under care of healthcare worker 330. While specific administering healthcare worker information 681 is shown as a list of data, the list is may include additional data elements or fewer than shown. Preferably the data includes the responsibilities or title 682 of the healthcare worker 330. Memory contents 680 can also include specific patient information 621 received from patient identification device 300 and final medication transaction report 660 received from information device 10.

The healthcare worker 330 is allowed to unlock the information device 10, and remove it and open portable container 100 by presenting their own administering healthcare worker information 681 to information device 10. When the portable container 100 and attached information device 10 are transported to the specific patient 360 and then brought close to healthcare worker identification device 320 (step 864), healthcare worker 330 presses activation button 16 (step 868). This causes information device 10 to transmit a signal that is received by healthcare worker identification device 320 (step 868). Healthcare worker identification device 320 responds by transmitting an authorization signal containing administering healthcare worker information 681 to information device 10 (step 872). The computer processor or comparison device 50 of the information device 10 compares portions of administering healthcare worker information 681 with corresponding elements of predetermined healthcare worker information 560 stored in the memory contents 500 of the information device (steps 876 and 880).). While the administering healthcare worker information 681 is stated to be transmitted to the information device 10 for comparison with predetermined healthcare worker information 560, it should be understood that this information could be transmitted to a different comparison device such as the patient identification device 300, information workstation 350 or computer peripheral device 355 for comparison.

When administering healthcare worker information 681 corresponds to predetermined healthcare worker information 560, information device 10 provides an approval tone using the audible alert device 18 to indicate that the medication in portable container 100 can be administered to patient 360 by healthcare worker 330, and latch release solenoid 90 is activated to enable securing latch 70 to be released by healthcare worker 330 (step 892). Once released, the alignment projection 24 of the information device 10 is removed from opening 126 so that the lid 122 of the container 100 can be moved to its open position 132.

The real time clock 66 in the information device 10 is used to record consumption time information 642 indicating when the medication is given or administered to patient 360 (step 896). This consumption time information 642 is recorded in the memory element 62 of the information device 10 as part of consumption information 640. Medication report 720 and universal resource locator 724 are modified to include predetermined healthcare worker information 560 in field 726 and consumption time information 642 in fields 728 and 729 to create a final medication report 730 and a final universal resource locator 734, part of medication report components 670.

Information device 10 may be used without latch release solenoid 90. Information device 10 has one or more sensors or switches 36 or 86 to detect when container 100 is being opened. Should the healthcare worker 330 attempt to open container 100 by depressing latch release button 74 before specific patient information 621 or administering healthcare worker information 681 is transmitted to information device 10, the first switch 86 will detect the partial retraction of securing latch 70 and sound an advisory alert via audible alert device 18. Healthcare worker 330 can then allow securing latch 70 to automatically close. Should healthcare worker 330 attempt to remove information device 10 from container 100 extra sensing switch 36 detects this and sounds a more pronounced alert tone. The information device will record the inappropriate opening of container 100 for reporting at a later time.

Medication Tracking System

Figure 31B:
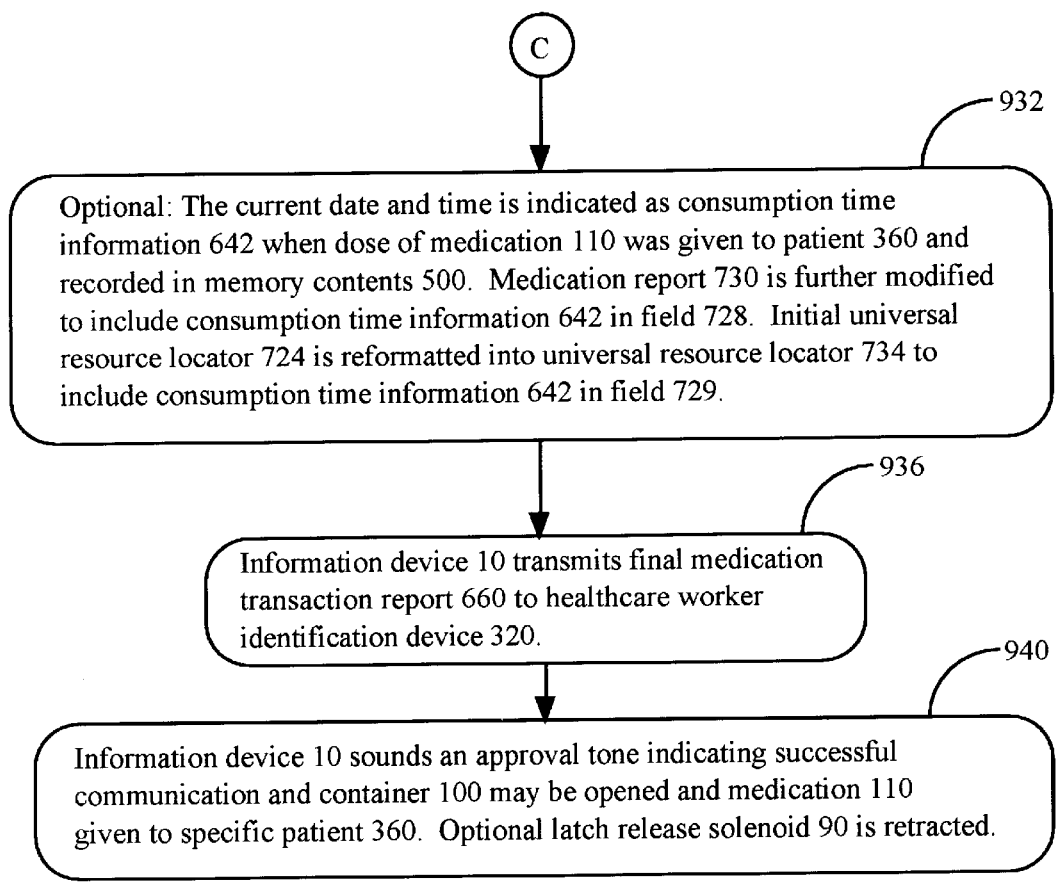

Information device can also be used as a medication tracking system. The healthcare worker 330 is allowed to unlock the information device 10, by presenting their own administering healthcare worker information 681 to information device 10. A flow chart showing a series of steps 910–940 for performing the medication tracking system is shown in FIGS. 31A–31B.

Medication 110 is dispensed into compartment 108 of container 100 for the predetermined patient using techniques discussed above (step 910). The portable container 100 and attached information device 10 are transported to the specific patient 360 (step 914) and then brought close to healthcare worker identification device 320. The healthcare worker 330 then presses activation button 16 (step 920). This causes information device 10 to transmit a signal that is received by the healthcare worker identification device 320 (step 924). Healthcare worker identification device 320 responds by transmitting an authorization signal containing administering healthcare worker information 681. Administering healthcare worker information 681 is received and is added to memory contents 500 and into field 726 of medication report 720 (step 928).

The real time clock 66 in information device 10 is used to record consumption time information 642 indicating when the medication is given or administered to patient 360 (step 932). This consumption time information 642 is recorded in the memory element 62 of the information device 10 as part of consumption information 640. Medication report 720 is further modified and universal resource locator 724 is modified to include consumption time information 642 in fields 728 and 729 to create a final universal resource locator 734 (step 932).

Information device 10 transmits final medication transaction report 660 to healthcare worker identification device 320 (step 936). Information device 10 provides an approval tone using audible alert device 18 to indicate a successful communication and that the medication in container 100 can be administered to a patient by healthcare worker 330, and the latch release solenoid 90 is activated to enable securing latch 70 to be released by healthcare worker 330 (step 940). Once released, the alignment projection 24 is pulled out of opening 126 so that lid 122 can be moved to open position 132.

Transferring Information from the Information Device to an Information System

Workstation 350 or computer peripheral device 355 is also adapted to receive memory contents 500, which can be formatted as final medication transaction report 660, for automatic transfer to pharmacy system 250 or hospital information system 260. This transfer can be done by using hospital network 240. While final medication transaction report 660 is shown as a list of data in FIG. 23, the list may include additional data elements or fewer than shown.

The data in the final medication transaction report 660 may be sent preformatted to comply with the structure of the data recording system, for example medication report 730 as shown in FIG. 26. Information device 10 may also format and transmit the address where memory contents 500 is to be stored. This may be in the form of universal resource locator (URL) 734 as shown in FIG. 27. In this case, workstation 350 need only send medication report 730 to the address indicated by universal resource locator 734 without interacting with workstation 350, thus keeping workstation 350 completely independent of needing to know how to handle medication report 730. Using the technology of the Internet, medication report 730 can be viewed on a display 740 of a workstation in a doctor's office, home or any workstation 220 or 350 as shown in FIG. 28. Using a browser or general purpose data retrieval, display and entry program medication report 730 may displayed by any workstation as seen in medication report browser presentation 744.

Information device 10 is returned to dispenser 204 for reuse. When this is done, memory contents 500, which can be formatted as final medication transaction report 660, is transmitted to dispenser 204 so that memory contents 500 can be communicated to pharmacy system 250 or hospital information system 260, via hospital network 240, and the information device 10 is considered available for reuse. Any error conditions, such as low battery voltage or communication errors, are also transmitted to dispenser 204 from information device 10.

Transferring Information from the Healthcare Worker Identification Device to an Information System The healthcare worker identification device 320 can also receive final medication transaction report 660 or components of it from information device 10. Final medication transaction report 660 can in turn be communicated to the workstation 350 by healthcare worker identification device 320 for communication to pharmacy database 254 or database 264 to automate the recording of the patient receiving.

Using Information Device to Label Medical Samples

The information device 10 can also be used to record patient information regarding blood, fluid, or tissue samples collected from the specific patient 360. The healthcare worker 330 obtains the samples directly from the specific patient 360, places them in compartment 108 and closes lid 122. Healthcare worker 330 then presses activation button 16, and information device 10 is placed in communication with the patient identification device 300 or workstation 350 associated with patient 360. In the same process as explained above, specific patient information 621 is transferred to information device 10. Healthcare worker 330 can manually press latch release button 74 and secure information device 10 to the container 100 to prevent the container from inappropriate opening. The container 100 holding the blood, fluid or tissue sample is then transferred to the appropriate laboratory for analysis. When received by the laboratory, specific patient information 621 is transferred from information device 10 by communicating with workstation 220, now placed in a laboratory setting, or a laboratory system (not shown). The laboratory will now know from which specific patient 360 the sample came.

While the invention has been described with reference to a preferred embodiment, it will be understood by those skilled in the art that various changes may be made and equivalents may be substituted without departing from the broader aspects of the invention.

I claim:

1. A patient verification method for verifying that a prescribed dose of medication is administered to a specific patient, said patient verification method comprising the steps of:

providing a dispensing workstation in communication with a database having predetermined patient information and corresponding prescribed medication dose information for each of a plurality of predetermined patients, a portable container adapted to move from open and closed positions and locked and unlocked positions, an information device having a memory, a comparison device, and a patient identification device associated with the specific patient, said patient identification device containing specific patient information;

using said dispensing workstation to select a selected patient from said database, said selected patient having selected patient information and corresponding selected prescribed medication dose information;

dispensing the prescribed dose of medication for said selected patient into said portable container, communicating a dispensing signal containing said selected patient information to said information device, storing said selected patient information in said memory of said information device, closing said portable container, attaching said information device to said portable container, and locking said portable container in said locked position;

transporting said portable container and information device to the specific patient;

communicating a verification signal containing either of said selected patient information and said specific patient information to said comparison device;

comparing said specific patient information to said selected patient information; and, unlocking said portable container when said specific patient information corresponds to said selected patient information.

2. The patient verification method of claim 1, and wherein said comparison device is a computer processor in said information device, and said verification signal contains said specific patient information.

3. The patient verification method of claim 2, and wherein the prescribed dose of medication is administered by a specific healthcare worker, said database includes predetermined healthcare worker information associated with said selected prescribed medication dose information, and said dispensing signal contains said predetermined healthcare worker information for storing in said memory of said information device, and further comprising the steps of:

providing a healthcare worker identification device containing administering healthcare worker information for the specific healthcare worker;

communicating an authorization signal containing said administering healthcare worker identification information to said information device; and, unlocking said portable container when said administering healthcare worker information corresponds to said predetermined healthcare worker information.

4. The patient verification method of claim 1, and wherein said dispensing workstation includes an automated dispensing machine with a bulk container adapted to hold the doses of medication, said dispensing workstation being in communication with said dispensing machine, and said dispensing machine being adapted to dispense the prescribed dose of medication into said portable container.

5. The patient verification method of claim 1, and wherein said dispensing signal contains selected prescribed medication dose information, said selected prescribed medication dose information being communicated to and stored in said memory of said information device, and further comprising the steps of:

determining when said portable container has been unlocked, and storing consumption information in said memory of said information device; and, communicating a confirmation signal containing said specific patient information, said selected prescribed medication dose information and said consumption information from said information device to either of said database and a separate database to confirm that the prescribed dose of medication was administered to the specific patient.

6. The patient verification method of claim 5, and wherein said selected prescribed medication dose information contains medication type and quantity information, and said confirmation signal contains said medication type and quantity information for updating either of said database and said separate database.

7. The patient verification method of claim 1, and wherein said portable container has first and second portions, said first portion having a compartment for holding the dose of medication and an opening for removing the dose of medication, and further comprising the step of sealing said portable container by moving said second portion from said open position to said closed position.

8. A patient verification method for verifying that a prescribed dose of medication is administered to a specific patient, said patient verification method comprising the steps of:

providing a dispensing workstation in communication with a database having predetermined patient information and corresponding prescribed medication dose information for each of a plurality of predetermined patients, a portable container, an information device having a memory, a comparison device, and a patient identification device associated with the specific patient, said patient identification device containing specific patient information;

using said dispensing workstation to select a selected patient from said database, said selected patient having selected patient information and corresponding selected prescribed medication dose information;

dispensing the prescribed dose of medication for said selected patient into said portable container, and communicating a dispensing signal containing said selected patient information to said information device, storing said selected patient information in said memory of said information device, and attaching said information device to said portable container;

transporting said portable container and information device to the specific patient;

communicating a verification signal containing either of said selected patient information and said specific patient information to said comparison device;

comparing said specific patient information to said selected patient information; and, activating an indicator when said specific patient information differs from said selected patient information.

9. The patient verification method of claim 8, and wherein said comparison device is a computer processor in said information device, and said verification signal contains said specific patient information.

10. The patient verification method of claim 9, and wherein the prescribed dose of medication is administered by a specific healthcare worker, said database includes predetermined healthcare worker information corresponding to said selected prescribed medication dose information, and said dispensing signal contains said healthcare worker information for storing in said memory of said information device, and further comprising the steps of:

providing a healthcare worker identification device containing administering healthcare worker information for the specific healthcare worker;

communicating an authorization signal containing said administering healthcare worker identification information from said healthcare worker identification device to said information device; and, unlocking said portable container when said administering healthcare worker information corresponds to said predetermined healthcare worker information.

11. The patient verification method of claim 8, and wherein said dispensing workstation includes an automated dispensing machine with a bulk container adapted to hold individual doses of medication, said dispensing workstation being in communication with said dispensing machine, and said dispensing machine being adapted to dispense the prescribed dose of medication into said portable container.

12. The patient verification method of claim 8, and wherein said portable container is adapted to move from open and closed positions and from locked and unlocked closed positions, and further comprising the steps of:

closing said portable container after the dose of medication has been dispensed into the portable container;

locking said portable container in said closed position to prevent access to the dose of medication; and, leaving said portable container locked when said specific patient information differs from said selected patient information.

13. The patient verification method of claim 12, and wherein said portable container has first and second portions, said first portion having a compartment for holding the prescribed dose of medication and an opening for removing the prescribed dose of medication, and further comprising the step of sealing said portable container by moving said second portion over said opening prior to locking said portable container in said closed position.

14. The patient verification method of claim 8, and wherein said portable container is adapted to move from open and closed positions, and said dispensing signal contains selected prescribed medication dose information for storage in said memory of said information device, and further comprising the steps of:

closing said portable container after the dose of medication has been dispensed into the portable container;

storing said specific patient information of said verification signal in said memory of said information device;

determining when said portable container is opened, and storing consumption information in said memory of said information device; and, communicating a confirmation signal containing said specific patient information, said selected prescribed medication dose information and said consumption information from said information device to either of said database of said dispensing workstation and a separate database to confirm that the medication was administered to the specific patient.

15. The patient verification method of claim 14, and wherein said selected prescribed medication dose information contains medication type and quantity information, and said confirmation signal contains said medication type and quantity information for updating said database.

16. A healthcare worker authorization method for ensuring an administering healthcare worker is authorized to administer a prescribed dose of medication to a specific patient, said healthcare worker authorization method comprising the steps of:

provviding a dispensing workstation in communication with a database having predetermined patient information and corresponding prescribed medication dose information for each of a plurality of predetermined patients, and said prescribed medication dose information being associated with predetermined healthcare worker information, a portable container adapted to move from open and closed positions, an information device having a memory, a healthcare worker identification device associated with the administering healthcare worker, said healthcare worker identification device containing administering healthcare worker information, and a comparison device for comparing said information;

using said dispensing workstation to select a selected patient from said database;

dispensing the prescribed dose of medication for said selected patient into said portable container, communicating a dispensing signal containing said predetermined healthcare worker information to said information device, and storing said predetermined healthcare worker information in said memory of said information device, attaching said information device to said portable container, and locking said portable container in said closed position;

transporting said portable container and information device to the specific patient;

communicating an authorization signal containing either of said predetermined healthcare worker information and said administering healthcare worker information to said comparison device;

comparing said administering healthcare worker information to said predetermined healthcare worker information; and, unlocking said portable container when said administering healthcare worker information matches said predetermined healthcare worker information.

17. The healthcare worker authorization method of claim 16, and wherein said comparison device is a computer processor in said information device, and said authorization signal contains said administering healthcare worker information.

18. A healthcare worker authorization method for ensuring an administering healthcare worker is authorized to administer a prescribed dose of medication to a specific patient, said healthcare worker authorization method comprising the steps of:

providing a dispensing workstation in communication with a database having predetermined patient information and corresponding prescribed medication dose information for each of a plurality of predetermined patients, said prescribed medication dose information being associated with predetermined healthcare worker information, a portable container, an information device having a memory, a healthcare worker identification device associated with the administering healthcare worker, said healthcare worker identification device containing administering healthcare worker information, and a comparison device for comparing said information;

using said dispensing workstation to select a selected patient from said database;

dispensing the prescribed dose of medication for said selected patient into said portable container, communicating a dispensing signal containing said predetermined healthcare worker information to said information device, storing said predetermined healthcare worker information in said memory of said information device, and attaching said information device to said portable container;

transporting said portable container and information device to the specific patient;

communicating an authorization signal containing either of said predetermined healthcare worker information and said administering healthcare worker information to said comparison device;

comparing said administering healthcare worker information to said predetermined healthcare worker information; and, activating an indicator when said administering healthcare worker information differs from said predetermined healthcare worker information.

19. The healthcare worker authorization method of claim 18, and wherein said comparison device is a computer processor in said information device, and said authorization signal contains said administering healthcare worker information.

20. A medication tracking method for a prescribed dose of medication administered to a specific patient by a healthcare worker, said medication tracking method comprising the steps of:

providing a dispensing workstation containing predetermined patient infringement and corresponding prescribed medication dose information for each of a plurality of predetermined patient, a portable container adapted to move from open and closed positions, an information device having a memory, a healthcare worker identification device associated with the administering healthcare worker, said healthcare worker identification device containing administering healthcare worker information, a patient identification device associated with the specific patient, said patient identification device containing specific patient information;

using said dispensing workstation to select a selected patient, said selected patient having selected patient information and corresponding selected prescribed medication dose information;

dispensing the prescribed dose of medication for said selected patient into said portable container, communicating a dispensing signal containing said selected medication dose information to said information device, storing said selected medication dose information in said memory of said information device, attaching said information device to said portable container, and moving said portable container to said closed position;

transporting said portable container and associated information device to the specific patient;

communicating an authorization signal from said healthcare worker identification device containing said administering healthcare worker information to and storing said administering healthcare worker information in said memory of said information device;

communicating a verification signal from said patient identification device containing said specific patient information to and storing said specific patient information in said memory of said information device;

moving said portable container to said open position after said administering healthcare worker information and specific patient information are received by said information device; and communicating a confirmation signal containing said selected medication dose information, said administering healthcare worker information and said specific patient information to either of said dispensing workstation and a separate database.

21. The medication tracking method of claim 20, and wherein said information device includes a clock, and further comprising the steps of:

obtaining consumption time information when said portable container is unlocked, and storing said consumption time information in said memory of said information device; and, including said consumption time information in said confirmation signal for communication to either of said database of said dispensing workstation and said separate database.

22. The medication tracking method of claim 20, and wherein said information device includes a data entry button, and further comprising the steps of:

entering consumption amount information via said data entry button, and storing said consumption time information in said memory of said information device; and, including said consumption amount information in said confirmation signal for communication to either of said database of said dispensing workstation and said separate database.

23. A patient verification apparatus for holding and limiting access to a prescribed dose of medication during transport to a specific patient, said patient verification apparatus comprising:

a portable container having first and second portions, said first portion having a compartment adapted to hold the medication during transport to the specific patient, and an opening for removing the medication, said second portion being adapted for movable engagement with said first portion to and from open and closed positions to selectively open and close said opening in said first portion;

a locking mechanism adapted to engage said second portion, said locking mechanism having a latch adapted to move between locked and unlocked positions, said locking mechanism being adapted to selectively lock said second portion in said closed position when said latch is in said locked position;

an information device attached to said portable container during transport to the specific patient, said information device having a communication device, a computer processor and a memory, said communication device and memory being in communication with said computer processor, said communication device being adapted to receive a dispensing signal containing selected patient information for storage in said memory;

a patient identification device containing specific patient information associated with the specific patient, said communication device being adapted to receive a verification signal containing said specific patient information from said patient identification device; and, wherein said computer processor of said information device compares said selected patient information to said specific patient information, said computer processor enabling said latch to move to said unlocked position and said second portion of said portable container being movable to said open position when said selected patient information corresponds to said specific patient information.

24. The patient verification apparatus of claim 23, and wherein said first and second portions of said container are separate pieces and said locking mechanism engages said first and second portions.

25. The patient verification apparatus of claim 23, and wherein said locking mechanism and said information device share a common housing.

26. The patient verification apparatus of claim 23, and further comprising a healthcare worker identification device containing administering healthcare worker information, and wherein said dispensing signal contains predetermined healthcare worker information for storage in said memory of said information device, and said communication device is adapted to receive an authorization signal containing said administering healthcare worker information, said computer processor enabling said latch to move from said locked position to said unlocked position when said predetermined healthcare worker information corresponds to said administering healthcare worker information.

27. The patient verification apparatus of claim 23, and wherein said communication device is adapted to transmit a confirmation signal containing consumption information to a database to confirm that the prescribed dose of medication was administered to the specific patient.

28. The patient verification apparatus of claim 27, and wherein said dispensing signal contains medication type and quantity information for storage in said memory, said database contains prescribed medication dose information, and said confirmation signal containing said medication type and quantity information is used to update said prescribed medication dose information.

29. The patient verification apparatus of claim 23, and wherein said patient identification device containing specific patient information is a bar code, and wherein said verification signal is received from said bar code.

30. The patient verification apparatus of claim 23, and wherein the medication is in liquid form and said portable container includes an IV bag.

31. A patient verification apparatus for verifying that a healthcare worker administers a prescribed dose of medication to a specific patient, said patient verification apparatus comprising:

a portable container adapted to hold the prescribed dose of medication during transport of the medication to the specific patient;

an information device attached to said portable container during transport to the specific patient, said information device having a communication device, a computer processor and a memory, said communication device and memory being in communication with said computer processor, said communication device being adapted to receive selected patient information for storage in said memory;

a patient identification device associated with the specific patient and containing specific patient information, said communication device being adapted to receive a verification signal containing said specific patient information, said computer processor comparing said selected patient information to said specific patient information; and, an indicator in communication with said information device, said computer processor activating said indicator after comparing said selected patient information to said specific patient information.

32. The patient verification apparatus of claim 31, and wherein said indicator includes an alarm, and said computer processor activates said alarm when said selected patient information differs from said specific patient information.

33. The patient verification apparatus of claim 31, and wherein said indicator includes a visual display, and said computer processor activates said visual display when said selected patient information corresponds to said specific patient information.

34. The patient verification apparatus of claim 31, and wherein said portable container has first and second portions, said first portion having a compartment adapted to hold the prescribed dose of medication and an opening for removing the prescribed dose of medication, said second portion being adapted for movable engagement with said first portion to and from open and closed positions to selectively open and close said opening, said computer processor enabling said second portion to move from said closed position to said open position when said selected patient information corresponds to said patient specific information.

35. The patient verification apparatus of claim 34, and wherein said second portion of said container is moved to said closed position after the prescribed dose of medication is dispensed into said compartment of said portable container, and further comprising a latch for locking said second portion in said closed position when said selected patient information differs from said specific patient information.

36. The patient verification apparatus of claim 34, and wherein said information device includes a clock and a sensor for detecting when said second portion of said container moves toward said open position, said sensor communicating said movement to said computer processor, said computer processor obtaining corresponding consumption time information from said clock and recording said consumption time information in said memory, and said communication device being further adapted to transmit a confirmation signal containing said specific patient information and said consumption time information to a database.

37. The patient verification apparatus of claim 36, and wherein said communication device is adapted to receive medication quantity information, said information device has a data entry button, said data entry button enables the healthcare worker to revise said medication quantity information based on actual consumption by the specific patient, and said confirmation signal contains said medication quantity information.

38. The patient verification apparatus of claim 31, and further comprising a dispensing workstation in communication with a database containing said predetermined patient information and corresponding prescribed medication dose information for each of a plurality of predetermined patients, said dispensing workstation having a computer processor, a communication device and an input terminal, said database, communication device, and input terminal being in communication with said computer processor, and said input terminal enabling the healthcare worker to select a selected patient from said database, said selected patient having selected prescription medication dose information, and said input terminal enabling the healthcare worker to transmit a dispensing signal containing said selected patient information to said communication device of said information device when the prescribed dose of medication is dispensed to said portable container.

39. The patient verification apparatus of claim 38, and wherein said dispensing workstation includes a dispensing machine having a bulk container adapted to hold the medication, and said computer processor of said dispensing workstation is in communication with and causes said automated dispensing machine to dispense the prescribed dose of medication from said bulk container to said portable container upon receipt of said prescribed medication dose information.

40. The patient verification apparatus of claim 38, and further including a healthcare worker identification device containing administering healthcare worker information, said memory of said dispensing workstation and said dispensing signal containing predetermined healthcare worker information, said communication device of said information device being adapted to receive an authorization signal containing said administering healthcare worker information from said healthcare worker identification device, said computer processor of said information device comparing said predetermined healthcare worker information to said administering healthcare worker information and activating said indicator when said predetermined healthcare worker information differs from said administering healthcare worker information.

41. The patient verification apparatus of claim 31, and wherein said patient identification device containing specific patient information is a bar code, and wherein said verification signal is received from said bar code.

42. The patient verification apparatus of claim 31, and wherein the medication is in liquid form and said portable container includes an IV bag.

43. A medication dispensing and tracking apparatus for tracking the administration of a prescribed dose of medication to a specific patient by a healthcare worker, said medication dispensing and tracking apparatus comprising:

a dispensing workstation in communication with a database containing predetermined patient information and corresponding prescribed medication dose information for each of a plurality of predetermined patients, said dispensing workstation having a first computer processor, a first communication device and an input terminal, said database, first communication device, and input terminal being in communication with said first computer processor, said input terminal enabling the healthcare worker to select a selected patient from said database, said selected patient having selected patient information and corresponding selected prescription medication dose information, and said input terminal enabling the healthcare worker to transmit said selected patient information and said selected prescribed medication dose information to said first communication device;

a portable container adapted to receive the prescribed dose of medication during transport to the specific patient, said portable container having first and second portions, said first portion having a compartment adapted to hold the prescribed dose of medication and an opening for removing the prescribed dose of medication, said second portion being movable to and from open and closed positions to selectively open and close said opening;

an information device attached to said portable container during transport to the specific patient, said information device having a second communication device, a second computer processor, a memory and a clock, said second communication device, memory and clock being in communication with said second computer processor, said second communication device being adapted to receive a dispensing signal from said first communication device, said dispensing signal containing said selected patient information and said selected prescribed medication dose information for storage in said memory, said second portion of said container being moved to said closed position when the prescribed dose of medication is dispensed into said portable container; and, a sensor for detecting when said second portion of said container moves from said closed position towards said open position and communicating said movement to said second computer processor, said second computer processor obtaining corresponding consumption time information from said clock and recording said consumption time information in said memory, and said second communication device being adapted to transmit a confirmation signal containing said selected patient information, said selected prescribed medication dose information and said consumption time information to either of said database and a separate database.

44. The medication dispensing and tracking apparatus of claim 43, and wherein said dispensing workstation includes a medication dispensing machine having a bulk medication container adapted to hold the doses of medication, said first computer processor being in communication with and causing said medication dispensing machine to dispense the prescribed dose of medication from said bulk medication container to said compartment of said portable container.

45. The medication dispensing and tracking apparatus of claim 43, and further comprising a patient identification device containing specific patient information associated with the specific patient and an alarm in communication with said second computer processor, said second communication device being adapted to receive a verification signal containing said specific patient information, said second computer processor comparing said selected patient information to said specific patient information, and said second computer processor activating said alarm when said selected patient information differs from said specific patient information.

46. The medication dispensing and tracking apparatus of claim 43, and further comprising a healthcare worker identification device containing administering healthcare worker information, and an alarm in communication with said second computer processor, said dispensing signal containing predetermined healthcare worker information, said second communication device being adapted to receive an authorization signal containing said administering healthcare worker information prior to said second portion of said container being moved toward said open position, said second computer processor comparing said predetermined healthcare worker information to said administering healthcare worker information, said second computer processor activating said alarm when said predetermined healthcare worker information differs from said administering healthcare worker information.

47. The medication and tracking apparatus of claim 43, and wherein said sensor is activated by a button.

48. A medication tracking apparatus for identifying a healthcare worker that administers a prescribed dose of medication to a specific patient, said medication tracking apparatus comprising:

a portable container having first and second portions, said first portion having a compartment adapted to hold the prescribed dose of medication during transport to the specific patient and an opening for removing the prescribed dose of medication, said second portion being movable to and from open and closed positions to selectively open and close said opening;

a locking mechanism adapted to engage said second portion, said locking mechanism having a latch adapted to move between locked and unlocked positions, said locking mechanism being adapted to selectively lock said second portion in said closed position when said latch is in said locked position;

a healthcare worker identification device containing administering healthcare worker information; and, an information device attached to said portable container during transport to the specific patient, said information device having a communication device, a computer processor and a memory, said communication device and said memory being in communication with said computer processor, said communication device being adapted to receive a dispensing signal containing selected patient information and corresponding selected prescribed medication dose information for storage in said memory; said communication device being further adapted to receive an authorization signal containing said administering healthcare worker information form said healthcare worker identification device, said computer processor enabling said latch to move from said locked position to said unlocked position upon receipt of said administering healthcare worker information.

49. The medication tracking apparatus of claim 48, and further comprising a dispensing workstation in communication with a database containing said predetermined patient information and said corresponding prescribed medication dose information for each of a plurality of predetermined patients, said dispensing workstation having a computer processor, a communication device and an input terminal, said database, communication device, and input terminal being in communication with said computer processor, said input terminal being adapted to enable the healthcare worker to select a selected patient from said database, said selected patient having selected patient information and corresponding selected prescription medication dose information, and said input device enabling the healthcare worker to transmit said dispensing signal containing said selected patient information and said selected prescribed medication dose information to said communication device of said information device.

50. The medication tracking apparatus of claim 49, and wherein said information device includes a clock and a sensor for detecting when said second portion of said container moves toward said open position, said sensor communicating said movement to said computer processor, said computer processor obtaining corresponding consumption time information from said clock and recording said consumption time information in said memory, said communication device being adapted to transmit a confirmation signal containing said consumption time information to a database.

51. The medication tracking apparatus of claim 48, and further comprising a patient identification device containing specific patient information associated with the specific patient, said communication device of said information device being adapted to receive a verification signal containing said specific patient information, and an indicator in communication with said computer processor, said computer processor activating said indicator upon comparing said selected patient information to said specific patient information.

52. The medication tracking apparatus of claim 51, and wherein said indicator includes an alarm, and said computer processor activates said alarm when said selected patient information differs from said specific patient information.

53. The medication tracking apparatus of claim 51, and wherein said indicator includes a visual display, and said computer processor activates said visual display when said selected patient information corresponds to said specific patient information.

54. The medication tracking apparatus of claim 48, and wherein said information device has a data entry button and said prescribed medication dose information contains quantity information, and said data entry button enables the healthcare worker to revise said quantity information based on actual consumption by the specific patient.

55. The medication tracking apparatus of claim 21, and wherein said healthcare worker identification device containing healthcare worker information is a bar code, and wherein said verification signal is received from said bar code.

56. The medication tracking apparatus of claim 48, and wherein the medication is in liquid form and said portable container includes an IV bag.

57. A healthcare worker authorization apparatus for verifying that a healthcare worker is authorized to administer a prescribed dose of medication to a specific patient, said healthcare worker authorization apparatus comprising:

- a portable container adapted to hold the prescribed dose of medication during transport to the specific patient;
- an information device attached to said portable container during transport to the specific patient, said information device having a communication device, a computer processor and a memory, said communication device and memory being in communication with said computer processor, said communication device being adapted to receive predetermined healthcare worker information for storage in said memory;
- a healthcare worker identification device associated with the specific healthcare worker and containing administering healthcare worker information, said communication device being adapted to receive an authorization signal containing said specific healthcare worker information, said computer processor comparing said predetermined healthcare worker information to said administering healthcare worker information; and,
- an indicator in communication with said information device, said computer processor activating said indicator after comparing said predetermined healthcare worker information to said administering healthcare worker information.

58. The healthcare worker authorization apparatus of claim 57, and wherein said indicator includes an alarm, and said computer processor activates said alarm when said predetermined healthcare worker information differs from said administering healthcare worker information.

59. The healthcare worker authorization apparatus of claim 57, and wherein said indicator includes a visual display, and said computer processor activates said visual display when said predetermined healthcare worker information corresponds to said administering healthcare worker information.

60. The healthcare worker authorization apparatus of claim 57, and wherein said portable container has first and second portions, said first portion having a compartment adapted to hold the prescribed dose of medication and an opening for removing the prescribed dose of medication, said second portion being adapted for movable engagement with said first portion to and from open and closed positions to selectively open and close said opening, said computer processor enabling said second portion to move from said closed position to said open position when said predetermined healthcare worker information corresponds to said administering healthcare worker information.

61. The healthcare worker authorization apparatus of claim 31, and wherein said information device includes a clock and a sensor for detecting when said second portion of said container moves toward said open position, said sensor communicating said movement to said computer processor, said computer processor obtaining corresponding consumption time information from said clock and recording said consumption time information in said memory, and said communication device being adapted to transmit a confirmation signal containing said administering healthcare worker information and said consumption time information to a database.

62. The healthcare worker authorization apparatus of claim 60, and wherein said second portion of said container is moved to said closed position after the prescribed dose of medication is dispensed into said compartment of said portable container, and further comprising a latch for locking said second portion in said closed position and preventing said second portion from moving to said open position when said predetermined healthcare worker information differs from said administering healthcare worker information.

63. The healthcare worker authorization apparatus of claim 57, and wherein said communication device is adapted to receive medication quantity information, said information device has a data entry button, and said data entry button is adapted to enable the healthcare worker to revise said medication quantity information based on actual consumption by the specific patient.

64. The healthcare worker authorization apparatus of claim 57, and further comprising a dispensing workstation in communication with a database containing predetermined healthcare worker information and corresponding prescribed medication dose information for each of a plurality of predetermined patients, said dispensing workstation having a computer processor, a communication device and an input terminal, said database, communication device, and input terminal being in communication with said computer processor, and said input terminal enabling the healthcare worker to transmit a dispensing signal containing said predetermined healthcare worker information to said communication device of said information device.

65. The healthcare worker authorization apparatus of claim 64, and wherein said dispensing workstation includes a dispensing machine having a bulk medication container adapted to hold the medication, and said computer processor of said dispensing workstation is in communication with and causes said dispensing machine to dispense the prescribed dose of medication from said bulk medication container to said portable container.

66. The healthcare worker authorization apparatus of claim 64, and further including a patient identification device containing specific patient information, said dispensing signal containing selected patient information, said communication device of said information device being adapted to receive a verification signal containing said specific patient information, said computer processor of said information device comparing said selected patient information to said specific patient information and activating said indicator when said selected patient information differs from said specific patient information.

67. The healthcare worker authorization apparatus of claim 57, and wherein said healthcare worker identification device containing administering healthcare worker information is a bar code, and wherein said verification signal is received from said bar code.

68. The healthcare worker authorization apparatus of claim 57, and wherein the medication is in liquid form and said portable container includes an IV bag.

* * * * *